US008080381B2

(12) United States Patent
Yamamoto et al.

(10) Patent No.: US 8,080,381 B2
(45) Date of Patent: Dec. 20, 2011

(54) INFECTIOUS ETIOLOGIC AGENT DETECTION PROBE AND PROBE SET, CARRIER, AND GENETIC SCREENING METHOD

(75) Inventors: Nobuko Yamamoto, Kanagawa (JP); Masaya Ogura, Tokyo (JP); Masahiro Kawaguchi, Kanagawa (JP); Mamoru Tsukada, Kanagawa (JP); Hiroto Yoshii, Tokyo (JP); Tomohiro Suzuki, Kanagawa (JP); Mie Ishii, Tokyo (JP); Toshifumi Fukui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1231 days.

(21) Appl. No.: 10/810,550

(22) Filed: Mar. 29, 2004

(65) Prior Publication Data

US 2004/0241643 A1  Dec. 2, 2004

(30) Foreign Application Priority Data

| Apr. 2, 2003 | (JP) | 2003-099452 |
|---|---|---|
| Apr. 2, 2003 | (JP) | 2003-099453 |
| Apr. 2, 2003 | (JP) | 2003-099454 |
| Apr. 2, 2003 | (JP) | 2003-099455 |
| Apr. 2, 2003 | (JP) | 2003-099456 |
| Apr. 2, 2003 | (JP) | 2003-099457 |
| Apr. 2, 2003 | (JP) | 2003-099458 |
| Apr. 2, 2003 | (JP) | 2003-099459 |
| Apr. 2, 2003 | (JP) | 2003-099460 |
| Apr. 2, 2003 | (JP) | 2003-099461 |
| Apr. 2, 2003 | (JP) | 2003-099462 |
| Apr. 2, 2003 | (JP) | 2004-099463 |
| Mar. 17, 2004 | (JP) | 2004-077045 |

(51) Int. Cl.
*C12Q 1/68* (2006.01)
*C07H 21/04* (2006.01)
*C12M 1/34* (2006.01)

(52) U.S. Cl. .................. 435/6.15; 435/6.11; 435/287.2; 536/24.32

(58) Field of Classification Search ........................ None
See application file for complete search history.

(56) References Cited

U.S. PATENT DOCUMENTS

| 5,474,796 A * | 12/1995 | Brennan ...................... 427/2.13 |
|---|---|---|
| 5,620,847 A | 4/1997 | Greisen et al. ................... 435/6 |
| 5,635,348 A | 6/1997 | Leong ............................. 435/6 |
| 5,708,159 A | 1/1998 | Ohno et al. ................. 536/24.32 |
| 5,723,344 A | 3/1998 | Mabilat et al. ................ 436/518 |
| 5,738,987 A | 4/1998 | Milliman ........................ 435/6 |
| 5,763,188 A | 6/1998 | Ohno et al. ...................... 435/6 |
| 6,001,558 A | 12/1999 | Backus et al. |
| 6,376,186 B1 * | 4/2002 | Hogan et al. ..................... 435/6 |
| 6,380,370 B1 | 4/2002 | Doucette-Stamm et al. 536/23.1 |
| 6,476,215 B1 | 11/2002 | Okamoto et al. ........... 536/25.3 |
| 6,551,776 B1 | 4/2003 | Grimont et al. ................... 435/6 |
| 7,035,738 B2 | 4/2006 | Matsumoto et al. |
| 7,169,555 B2 | 1/2007 | Stüber et al. ..................... 435/6 |
| 7,283,912 B2 * | 10/2007 | Yoshii et al. ................... 702/20 |
| 7,291,724 B2 | 11/2007 | Stüber et al. ............... 536/24.32 |
| 2002/0160401 A1 | 10/2002 | Nozaki et al. .................... 435/6 |
| 2004/0010129 A1 * | 1/2004 | Hsu et al. .................... 536/23.1 |
| 2004/0185459 A1 | 9/2004 | Otsuka et al. .................... 435/6 |

FOREIGN PATENT DOCUMENTS

| DE | 199 15 141 | 9/2000 |
|---|---|---|
| DE | 199 41 359 | 3/2001 |
| EP | 0 497 464 | 1/1992 |
| EP | 0 957 175 | 4/1998 |
| JP | 6-133798 | 5/1994 |
| JP | 7/39398 | 2/1995 |
| JP | 9-505556 A | 6/1997 |
| JP | 10-304896 | 11/1998 |
| JP | 10-304897 | 11/1998 |
| JP | 11-69987 A | 3/1999 |
| JP | 11-187900 | 7/1999 |
| JP | 2000-135085 | 5/2000 |

(Continued)

OTHER PUBLICATIONS

Wang, R., et al., "Design and evaluation of oligonucleotide-microarray method for the detection of human intestinal bacterial in fecal samples", FEMS Microbiology Letters, vol. 213, pp. 175 to 182 (2002).
Wilson, K., et al., "High-Density Microarray of Small-Subunit Ribosomal DNA Probes", Applied and Environmental Microbiology, pp. 2535 to 2541 (2002).
Krimmer, V., et al., "Detection of *Staphylococcus aureus* and *Staphylococcus epidermidis* in Clinical Samples by 16S rRNA-Directed In Situ Hybridization", Journal of Clinical Microbiology, pp. 2667 to 2673 (1999).

(Continued)

*Primary Examiner* — Diana Johannsen
(74) *Attorney, Agent, or Firm* — Fitzpatrick, Cella, Harper & Scinto

(57) ABSTRACT

An infectious etiologic agent detection probe set which detects an infectious etiologic agent gene, includes a plurality of kinds of probes including oligonucleotide having base sequences selected from each of a plurality of groups selected from a first group including base sequences of SEQ ID Nos. 1 to 14 and complementary sequences thereof, a second group including base sequences of SEQ ID Nos. 15 to 24 and complementary sequences thereof, a third group including base sequences of SEQ ID Nos. 25 to 36 and complementary sequences thereof, a fourth group including base sequences of SEQ ID Nos. 37 to 47 and complementary sequences thereof, a fifth group including base sequences of SEQ ID Nos. 48 to 57 and complementary sequences thereof, a sixth group including base sequences of SEQ ID Nos. 58 to 68 and complementary sequences thereof, a seventh group including base sequences of SEQ ID Nos. 69 to 77 and complementary sequences thereof, an eighth group including base sequences of SEQ ID Nos. 78 to 85 and complementary sequences thereof, a ninth group including base sequences of SEQ ID Nos. 86 to 97 and complementary sequences thereof, and a 10th group including base sequences of SEQ ID Nos. 98 to 106 and complementary sequences thereof.

6 Claims, No Drawings

FOREIGN PATENT DOCUMENTS

| | | |
|---|---|---|
| JP | 2001-136969 | 3/2001 |
| JP | 2001-299396 | 10/2001 |
| JP | 2002-51783 | 2/2002 |
| JP | 2002-238563 | 8/2002 |
| JP | 2002-330768 | 11/2002 |
| JP | 2002-345480 A | 12/2002 |
| JP | 2002-355084 | 12/2002 |
| JP | 2002-542808 | 12/2002 |
| WO | 95/05391 A1 | 2/1995 |
| WO | 95/20055 | 7/1995 |
| WO | 96/16186 | 5/1996 |
| WO | 97/21819 | 6/1997 |
| WO | 97/31114 | 8/1997 |
| WO | 98/14567 | 4/1998 |
| WO | 99/07722 | 2/1999 |
| WO | 99/22023 | 5/1999 |
| WO | 00/58505 | 10/2000 |
| WO | 00/66788 | 11/2000 |
| WO | 00/66789 | 11/2000 |
| WO | 01/07648 | 2/2001 |
| WO | 01/34809 | 5/2001 |
| WO | 01/42457 | 6/2001 |
| WO | 01/48237 | 7/2001 |
| WO | 02/02794 | 1/2002 |
| WO | 02/02811 | 1/2002 |
| WO | 02/070728 | 9/2002 |
| WO | 02/086160 | 10/2002 |
| WO | 03/012042 A2 | 2/2003 |
| WO | 97/41253 | 11/2006 |

OTHER PUBLICATIONS

Database EMBL Accession No. AJ489358, "*Staphylococcus* sp. Lgg15.2 partial 16S rRNA gene, strain Lgg15.2 16S ribosomal RNA; 16S rRNA gene; *Staphylococcus* sp. Lgg15.2" Jun. 13, 2002.
Database EMBL Accession No. AF498067, "Uncultured *Staphylococcus* sp. isolate DGGE gel band M4 16S ribosomal RNA gene, partial sequence" Apr. 26, 2002.
Database EMBL Accession No. AY072700, "*Bacillus pumilus* strain ID48 16S ribosomal RNA gene, partial sequence" Jan. 29, 2002.
Database EMBL Accession No. AF076039, "*Pseudomonas aeruginosa* 16S ribosomal RNA gene, partial sequence" Sep. 9, 1998.
Database EMBL Accession No. AB061685, "*Serratia marcescens* gene for 16S rRNA, partial sequence" May 16, 2001.
Database EMBL Accession No. AJ296306, "*Serratia marcescens* 16S rRNA gene, isolate 90-166" Nov. 27, 2000.
Database EMBL Accession No. AB002522, "*Streptococcus pneumoniae* DNA for 16S rRNA, strain MAFF 911410" Apr. 13, 1997.
Database EMBL Accession No. AF076029, "*Streptococcus pneumoniae* 16S ribosomal RNA gene, partial sequence" Sep. 9, 1998.
Database EMBL Accession No. X87977, "*H. influenzae*DNA for ribosomal RNA (strain CIP 5483)" Jun. 25, 1996.
Database EMBL Accession No. M35019 M59433, "*H. influenzai* 16S ribosomal RNA" Mar. 12, 1991.
Database EMBL Accession No. Y11487, "*K.pneumoniae* ribosomal RNA, strain ATCC13883" Feb. 27, 1997.
Database EMBL Accession No. Y17668, "*Kiebsiella pneumoniae* 16S rRNA gene, strain Klebs313, partial" Jun. 29, 1998.
Database EMBL Accession No. X80721, "*E.coli* rrnA gene" Mar. 29, 1996.
Database EMBL Accession No. AE016749 AE015929, "*Staphylococcus epidermidis* ATCC 12228, section 6 of 9 of the complete genome" Jan. 2, 2003.
Database EMBL Accession No. D83363, "*Staphylococcus epidermidis* (strain ATCC 14990T) gene for 16S rRNA, partial sequence" Feb. 27, 1996.
Database EMBL Accession No. AAX24989, "*E. coli* MG1655 rrnH operon (16S-spacer-23S-spacer-5S0" Jul. 24, 1999.
Database EMBL Accession No. AF157695, "*Enterobacter cloacae* 16S ribosomal RNA gene, partial sequence" Jun. 28, 1999.
Database EMBL Accession No. AJ420803, "*Enterococcus faecalis* 16S rRNA gene, strain CECT481T" Dec. 21, 2001.
Database EMBL Accession No. U11775, "*Staphylococcus aureus* methicillin resistant isolate H11 clone RRNV13 16S-23S rRNA spacer region" Feb. 21, 1995.
Database EMBL Accession No. U33121, "*Klebsiella pneumoniae* 16S ribosomal RNA gene" Aug. 27, 1996.
Yu Huimin, et al., "Detection of bacterial DNA by polymerase chain reaction and reverse hybridization of 16SrRNA gene", Chinese Journal of Practical Pediatrics, 2000, vol. 15, No. 2, pp. 97-99.
Samuel Yang, et al., "Quantitative Multiprobe PCR Assay for Simultaneous Detection and Identification to Species Level of Bacterial Pathogens", Journal of Clinical Microbiology, vol. 40, No. 9, 2002, pp. 3449-3454.
GenBank, Accession No. AR206315, Jun. 20, 2002.
Database EMBL Accession No. AY126146, *Staphylococcus aureus* strain R1 16S ribosomal RNA gene, partial sequence, Jul. 25, 2002.
Database EMBL Accession No. AAL44979, "Enterobacter 16S rRNA gene fragment", Nov. 20, 2001.
Harada, et al., GenBank Accession No. AB004753, Jun. 20, 1997.
GenBank, Accession No. PAZ76651, Mar. 25, 1997.
Fujita, et al, "Comparison of Antimicrobial Activity of Cefotaxime With That of Other Several Cephems Against Recent Clinical Isolates"; The Japanese Journal of Antibiotics, XXXVI-10, Oct. 1983, pp. 2887-2892 (with English-language abstract).

* cited by examiner

INFECTIOUS ETIOLOGIC AGENT DETECTION PROBE AND PROBE SET, CARRIER, AND GENETIC SCREENING METHOD

FIELD OF THE INVENTION

The present invention relates to detection and/or identification of an infectious etiologic agent as an etiologic agent of an infectious disease and, more particularly, to a probe and probe set originated in an infectious etiologic agent, a carrier, and a genetic screening method, which are useful for detection and identification of the etiologic agent of an infectious disease.

The present invention also relates to a PCR amplification process of an infectious etiologic agent, which is suitable for detection and/or identification of an infectious etiologic agent.

BACKGROUND OF THE INVENTION

In recent years, gene expression analysis using DNA chips (also referred to as DNA microarrays hereinafter) is done in various fields including drug development. Different specimen DNAs are made to react with a DNA microarray in which various kinds of gene sets (probes) are arranged. Gene dosages which exist in the respective specimens are compared. Genes which are present in high dosages (the expression amounts are large) or inactive genes (the expression amounts are small) at each stage are classified and analyzed in association with functions.

An example is an infectious etiologic agent test. In Japanese Patent Laid-Open No. 2001-299396, Ezaki et al have proposed a microorganism identification method using, as a DNA probe, a DNA chip on which chromosome DNAs are immobilized. According to this method, a plurality of chromosome DNAs originated in a plurality of known microorganisms with different GC contents are made to react with chromosome DNAs originated in an unknown microorganism in a specimen. When the resultant hybridization complex is detected, the unknown microorganism in the specimen can be detected.

As probes used for DNA chips for infectious etiologic agent tests, Ono et al have proposed a bacterial detection probe using restriction enzyme fragments in Japanese Patent Laid-Open No. 6-133798, a Pseudomonas aeruginosa detection probe in Japanese Patent Laid-Open No. 10-304896, and a detection probe using restriction enzyme fragments of Escherichia coli, klebsiella pneumoniae, and *Enterobacter cloacae* in Japanese Patent Laid-Open No. 10-304897.

As a microarray, for example, a microarray using stamping called a Stanford method is known. For example, DNA chips on which cDNA fragments of known genes of human origin, which are related to cancers, are applied by spotting or stamping and chips prepared by bonding cDNA fragments of 1,000 kinds of known genes of human origin to slide glasses are commercially available from TAKARA SHUZO.

On the other hand, a chip available from Affymetrix is prepared by designing an oligonucleotide probe set on the basis of the known gene cDNAs, and probes are laid out by synthesis on a substrate. Oligoprobes are laid out on one chip at a high density so that the expression levels of 10,000 or more genes can be analyzed at once.

However, the DNA chips of the prior arts described above use DNA probes such as chromosome DNAs or restriction enzyme fragments. DNAs directly extracted from microorganisms are used as materials. For this reason, the chips can hardly be mass-prepared at a time and are not suitable for clinical diagnosis. For application to clinical diagnosis, mass production of inexpensive and uniform DNA chips is necessary. For this purpose, mass preparation of uniform DNAs as probe solutions is essential. However, mass preparation of DNA probes is impossible. Even for DNA probes, when PCR amplification reaction is used, the number of DNAs can gradually be increased. However, mass preparation at a time using the PCR reaction is difficult, and the DNA chips are difficult to use for clinical diagnosis.

In addition, since the base length of a DNA probe is large, it is difficult to identify one species in similar species. Such a DNA probe is therefore not suitable for, e.g., infection detection. In treating an infection, the species must be specified, and antibiotic drugs corresponding to it must be selected and administered. For this purpose, an infection detection probe is required to have a function capable of detecting a species while discriminating similar species, although bacteria belonging to the same species need not accurately be discriminated (that is, bacteria in the same species can be detected all together). However, in, e.g., the DNA chip using restriction enzyme fragments of *Escherichia coli, klebsiella pneumoniae*, and *Enterobacter cloacae*, which is disclosed in Japanese Patent Laid-Open No. 10-304897, cross reaction occurs between the three species because of the large base length of the probe. Since similar species cannot individually be discriminated, the DNA chip can hardly be used for infection detection.

As an application purpose of microarrays, infectious etiologic agent tests have received a great deal of attention. Some probe sets aiming at testing infectious etiologic agents have also been proposed.

As an important point of bacterial tests using microarrays, detection must be possible even when the number of infectious etiologic agents is small. To do this, it is effective to amplify specific parts in the base sequences of the DNAs of infectious etiologic agents by, e.g., PCR reaction using primers. For example, a 16s rRNA gene arrangement contains a sequence unique to the species in the information of about 1,700 base pairs. When the sequence is used, classification can be done to some extent. In detecting/identifying bacteria, 16s rRNA parts in the DNA base sequences of bacteria are preferably used. Hence, it is demanded to amplify the 16s rRNA parts.

For various kinds of bacteria, however, the gene arrangements are only partially clarified, and the 16s rRNAs are not totally known. For this reason, it is not easy to design primers for PCR amplification reaction.

SUMMARY OF THE INVENTION

The present invention has been made in consideration of the above situation, and has as its object to provide an infection detection probe which allows mass preparation at a time and identification of a species in similar species.

More specifically, it is an object of the present invention to provide an infection detection probe which can suitably be used to classify a plurality of kinds of etiologic agents of an infection on the basis of the species.

It is another object of the present invention to provide a probe set which also considers the stability of a hybrid body between an infection detection probe and a specimen so that the difference between similar species can accurately be evaluated on a DNA chip.

It is still another object of the present invention to provide a carrier on which the infection detection probe is immobilized to make the infection detection probe react with the specimen.

It is still another object of the present invention to provide a carrier on which the infection detection probes are chemically immobilized so that the infection detection probes are stably immobilized on the carrier, and a detection result with high reproducibility can be obtained in the process of reaction with a specimen solution.

It is still another object of the present invention to provide a PCR reaction primer which amplifies the 16s rRNAs of an etiologic agent in a specimen in order to detect and/or identify an infectious etiologic agent.

It is still another object of the present invention to provide a primer set which can commonly be used for a plurality of species and effectively amplify the 16s rRNAs of an etiologic agent even when the species is unknown.

It is still another object of the present invention to provide a primer set which can amplify the 16s rRNAs of a plurality of kinds of etiologic agents under the same PCR conditions.

The present invention provides a primer set characterized by amplifying all species without amplifying genes originated in human genomes by causing PCR reaction for a human blood specimen by using all the primer sets simultaneously. More specifically, a primer set having a sequence which is different from the base sequence of human genome genes by three or more bases is proposed.

Other features and advantages of the present invention will be apparent from the following description.

DETAILED DESCRIPTION OF THE PREFERRED EMBODIMENT

A preferred embodiment of the present invention will now be described in.

In the following embodiment, an oligonucleotide probe used to identify the etiologic agent of an infection and, more specifically, a probe used to detect one or some of *Staphylococcus aureus, Staphylococcus epidermidis, Escherichia coli, Klebsiella pneumoniae, Pseudomonas aeruginosa, Serratia marcescens, Streptococcus pneumoniae, Haemophilus influenzae, Enterobacter cloacae*, and *Enterococcus faecalis* will be described. That is, a nucleic acid probe or nucleic acid probe set, which is used to detect rRNA gene arrangements in the genes of the above 10 infectious etiologic agents in proper quantities, is disclosed.

According to this embodiment, the oligonucleotide probe to be reacted with a specimen solution containing the nucleic acid sequence of the genes of the infectious etiologic agents contains one base sequence which belongs to one of the first group (SEQ ID Nos. 1 to 14 in the attached sequence table) shown in Table 1, the second group (SEQ ID Nos. 15 to 24) shown in Table 2, the third group (SEQ ID Nos. 25 to 36) shown in Table 3, the fourth group (SEQ ID Nos. 37 to 47) shown in Table 4, the fifth group (SEQ ID Nos. 48 to 57) shown in Table 5, the sixth group (SEQ ID Nos. 58 to 68) shown in Table 6, the seventh group (SEQ ID Nos. 69 to 77) shown in Table 7, the eighth group (SEQ ID Nos. 78 to 85) shown in Table 8, the ninth group (SEQ ID Nos. 86 to 97) shown in Table 9, and the 10th group (SEQ ID Nos. 98 to 106) shown in Table 10 (to be described later). An oligonucleotide probe having a base sequence selected from the first group detects *Staphylococcus aureus*. An oligonucleotide probe having a base sequence selected from the second group detects *Staphylococcus epidermidis*. An oligonucleotide probe having a base sequence selected from the third group detects *Escherichia coli*. An oligonucleotide probe having a base sequence selected from the fourth group detects *Klebsiella pneumoniae*. An oligonucleotide probe having a base sequence selected from the fifth group detects *Pseudomonas aeruginosa*. An oligonucleotide probe having a base sequence selected from the sixth group detects *Serratia marcescens*. An oligonucleotide probe having a base sequence selected from the seventh group detects *Streptococcus pneumoniae*. An oligonucleotide probe having a base sequence selected from the eighth group detects *Haemophilus influenzae*. An oligonucleotide probe having a base sequence selected from the ninth group detects *Enterobacter cloacae*. An oligonucleotide probe having a base sequence selected from the 10th group detects *Enterococcus faecalis*.

Complementary sequences of these probe sequences can also be used as effective probe sequences because they have the same functions as those of the above probe sequences (the complementary sequences of the first group are indicated by SEQ ID Nos. 113 to 126 in the attached sequence table, the complementary sequences of the second group are indicated by SEQ ID Nos. 127 to 136, the complementary sequences of the third group are indicated by SEQ ID Nos. 137 to 148, the complementary sequences of the fourth group are indicated by SEQ ID Nos. 149 to 159, the complementary sequences of the fifth group are indicated by SEQ ID Nos. 160 to 169, the complementary sequences of the sixth group are indicated by SEQ ID Nos. 170 to 180, the complementary sequences of the seventh group are indicated by SEQ ID Nos. 181 to 189, the complementary sequences of the eighth group are indicated by SEQ ID Nos. 190 to 197, the complementary sequences of the ninth group are indicated by SEQ ID Nos. 198 to 209, and the complementary sequences of the 10th group are indicated by SEQ ID Nos. 210 to 218).

The probes for the respective bacteria were designed from the genome parts coding the 16s rRNAs such that they could have a very high specificity with respect to the corresponding bacteria, any variation between the probe base sequences could be prevented, and a sufficient hybridization sensitivity could be expected.

These oligonucleotide probes are designed such that a stable hybrid body is formed by hybridization reaction between a specimen and two or more kinds of probes bonded onto a carrier, and a satisfactory result can be obtained.

As a characteristic feature, the carrier according to the present invention, on which the infection detection probe of the present invention is immobilized, is prepared by discharging oligonucleotide by using a BJ printer and chemically bonding it to the carrier. As compared to the prior arts, the probe hardly peels off. An additional effect for increasing the sensitivity is also obtained. When a DNA chip is produced by stamping called a Stanford method that is generally widely used (for example, TAKARA SHUZO produces DNA chips by applying cDNA fragments of known genes of human origin, which are related to cancers, by spotting or stamping), the applied DNA readily peels off. In addition, when a probe is laid out on a DNA chip by synthesis, as in the prior art (e.g., the DNA chip available from Affymetrix), accurate evaluation is impossible because the synthesis yield changes between probe sequences. The carrier according to the present invention is prepared also in consideration of these problems. As its characteristic features, the probe is stably immobilized and hardly peels off, as compared to the prior arts, and highly sensitive and accurate detection can be executed. The preferred embodiment of the present invention will be described below in detail.

The DNA chip of this embodiment can be applied to any specimen in which bacteria may be present, and for example, body fluids originated in animals such as human and livestock, including blood, spinal fluid, phlegm, stomach fluid, vaginal discharge, and intraoral mucus, and excretion such as urine and feces. All media which can be contaminated by bacteria can also be subjected to a test using the DNA chip, including food, drink water and hot spring water in the natural environment, which may cause food poisoning by contamination, filters from air and water cleaners, and so forth. Animals and plants which should be quarantined in import/export are also used as specimens.

The specimens used for the DNA chip of this embodiment include not only an extracted nucleic acid itself but also specimens prepared by various methods, such as an amplified specimen prepared by using an PCR reaction primer designed for 16s rRNA detection, a specimen prepared by causing PCR reaction on the basis of a PCR amplified product, a specimen prepared by an amplification method other than PCR, and a specimen labeled by various labeling methods for visualization.

The carrier used for the DNA chip of this embodiment includes all sorts of carriers including flat substrates such as a glass substrate, a plastic substrate, and a silicon wafer, a three-dimensional structure having a three-dimensional pattern, a spherical body such as a bead, and rod-, cord-, and thread-shaped structures. The carrier also includes a substrate whose surface is processed such that a probe DNA can be immobilized. Especially, a carrier prepared by introducing a functional group to its surface to make chemical reaction possible has a preferable form from the viewpoint of reproducibility because the probe is stably bonded in the process of hybridization reaction.

As an example of the immobilization method used in the present invention, a combination of a maleimide group and a thiol (—SH) group is used. More specifically, a thiol (—SH) group is bonded to the terminal of a nucleic acid probe, and a process is executed make the solid surface have a maleimide group. Accordingly, the thiol group of the nucleic acid probe supplied to the solid surface reacts with the maleimide group on the solid surface to immobilize the nucleic acid probe.

To introduce the maleimide group, first, an aminosilane coupling agent is caused to react on a glass substrate. Next, the maleimide group is introduced by reaction between the amino group and an EMCS reagent (N-(6-Maleimidocaproyloxy)succinimide: available from Dojin). Introduction of the SH group to a DNA can be done by using 5'-Thiol-ModifierC6 (available from Glen Research) when the DNA is synthesized by an automatic DNA synthesizer.

Instead of the above-described combination of a thiol group and a maleimide group, a combination of, e.g., an epoxy group (in the solid phase) and an amino group (nucleic acid probe terminal) can also be used as a combination of functional groups to be used for immobilization. Surface treatments using various kinds of silane coupling agents are also effective. Oligonucleotide in which a functional group which can react with a functional group introduced by a silane coupling agent is introduced is used. A method of applying a resin having a functional group can also be used.

The present invention will be described below in more detail on the basis of examples using the infectious etiologic agent detection probes to be used to detect the 10 etiologic agents described above.

Example 1

Microorganism Detection Using 1-Step PCR

1. Preparation of Probe DNAs

Nucleic acid sequences shown in Tables 1 to 10 were designed as probes to be used for detection of the 10 etiologic agents. More specifically, the following probe base sequences were selected from the genome parts coding the 16s rRNAs of the respective bacteria. These probe base sequences were designed such that they could have a very high specificity with respect to the corresponding bacteria, any variation between the probe base sequences could be prevented, and a sufficient hybridization sensitivity could be expected (The probe base sequences need not always completely match those shown in Tables 1 to 10. Probe base sequences having base lengths of 20 to 30, including the probe base sequences, are also included in the probe base sequence shown in the tables. As described above, complementary sequences (complementary strands) of the base sequences shown in the tables may also be used).

In the following tables, "Probe No." is assigned for convenience. SEQ ID Nos. coincide with those in the attached sequence tables. As described above, the complementary strand sequences of the base sequences with SEQ ID Nos. 1 to 106 have SEQ ID Nos. 113 to 218.

TABLE 1

Probes for detecting *Staphylococcus aureus* strain

| Name of microorganizm | Probe No. | SEQ ID No. | Sequence |
|---|---|---|---|
| *Staphylococcus aureus* | PA-1 | 1 | 5' GAACCGCATGGTTCAAAAGTGAAAGA 3' |
| | PA-2 | 2 | 5' CACTTATAGATGGATCCGCGCTGC 3' |
| | PA-3 | 3 | 5' TGCACATCTTGACGGTACCTAATCAG 3' |
| | PA-4 | 4 | 5' CCCCTTAGTGCTGCAGCTAACG 3' |
| | PA-5 | 5 | 5' AATACAAAGGGCAGCGAAACCGC 3' |
| | PA-6 | 6 | 5' CCGGTGGAGTAACCTTTTAGGAGCT 3' |
| | PA-7 | 7 | 5' TAACCTTTTAGGAGCTAGCCGTCGA 3' |
| | PA-8 | 8 | 5' TTTAGGAGCTAGCCGTCGAAGGT 3' |
| | PA-9 | 9 | 5' TAGCCGTCGAAGGTGGGACAAAT 3' |

TABLE 1-continued

Probes for detecting *Staphylococcus aureus* strain

| Name of microorganizm | Probe No. | SEQ ID No. | Sequence |
|---|---|---|---|
| | PA-10 | 10 | 5' ACGGACGAGAAGCTTGCTTCTCT 3' |
| | PA-11 | 11 | 5' TGTCACTTATAGATGGATCCGCGCT 3' |
| | PA-12 | 12 | 5' TGTAAGTAACTGTGCACATCTTGACG 3' |
| | PA-13 | 13 | 5' ACAACTCTAGAGATAGAGCCTTCCCC 3' |
| | PA-14 | 14 | 5' GTGGAGTAACCTTTTAGGAGCTAGCC 3' |

TABLE 2

Probes for detecting *Staphylococcus epidermidis* strain

| Name of microorganizm | Probe No. | SEQ ID No. | Sequence |
|---|---|---|---|
| *Staphylococcus epidermidis* | PB-1 | 15 | 5' GAACAGACGAGGAGCTTGCTCC 3' |
| | PB-2 | 16 | 5' TAGTGAAAGACGGTTTTGCTGTCACT 3' |
| | PB-3 | 17 | 5' TAAGTAACTATGCACGTCTTGACGGT 3' |
| | PB-4 | 18 | 5' GACCCCTCTAGAGATAGAGTTTTCCC 3' |
| | PB-5 | 19 | 5' AGTAACCATTTGGAGCTAGCCGTC 3' |
| | PB-6 | 20 | 5' GAGCTTGCTCCTCTGACGTTAGC 3' |
| | PB-7 | 21 | 5' AGCCGGTGGAGTAACCATTTGG 3' |
| | PB-8 | 22 | 5' AGACGAGGAGCTTGCTCCTCTG 3' |
| | PB-9 | 23 | 5' AGAACAAATGTGTAAGTAACTATGCACGT 3' |
| | PB-10 | 24 | 5' ACCATTTGGAGCTAGCCGTCGA 3' |

TABLE 3

Probes for detecting *Escherichia coli* strain

| Name of microorganizm | Probe No. | SEQ ID No. | Sequence |
|---|---|---|---|
| *Escherichia coli* | PC-1 | 25 | 5' CTCTTGCCATCGGATGTGCCCA 3' |
| | PC-2 | 26 | 5' ATACCTTTGCTCATTGACGTTACCCG 3' |
| | PC-3 | 27 | 5' TTTGCTCATTGACGTTACCCGCAG 3' |
| | PC-4 | 28 | 5' ACTGGCAAGCTTGAGTCTCGTAGA 3' |
| | PC-5 | 29 | 5' ATACAAAGAGAAGCGACCTCGCG 3' |
| | PC-6 | 30 | 5' CGGACCTCATAAAGTGCGTCGTAGT 3' |
| | PC-7 | 31 | 5' GCGGGGAGGAAGGGAGTAAAGTTAAT 3' |
| | PC-8 | 32 | 5' TAACAGGAAGAAGCTTGCTTCTTTGCTG 3' |
| | PC-9 | 33 | 5' TTGCCATCGGATGTGCCCAGAT 3' |
| | PC-10 | 34 | 5' GGAAGGGAGTAAAGTTAATACCTTTGCTC 3' |
| | PC-11 | 35 | 5' ATCTTTTGTTGCCAGCGGTCCG 3' |
| | PC-12 | 36 | 5' AAGGGAGTAAAGTTAATACCTTTGCTCATTG 3' |

TABLE 4

Probes for detecting *Klebsiella pneumoniae* strain

| Name of microorganizm | Probe No. | SEQ ID No. | Sequence |
|---|---|---|---|
| *Klebsiella pneumoniae* | PD-1 | 37 | 5' TAGCACAGAGAGCTTGCTCTCGG 3' |
| | PD-2 | 38 | 5' TCATGCCATCAGATGTGCCCAGA 3' |
| | PD-3 | 39 | 5' CGGGGAGGAAGGCGATAAGGTTAAT 3' |
| | PD-4 | 40 | 5' TTCGATTGACGTTACCCGCAGAAGA 3' |
| | PD-5 | 41 | 5' GGTCTGTCAAGTCGGATGTGAAATCC 3' |
| | PD-6 | 42 | 5' GCAGGCTAGAGTCTTGTAGAGGGG 3' |
| | PD-7 | 43 | 5' TCATGCCATCAGATGTGCCCAGAT 3' |
| | PD-8 | 44 | 5' CGGGGAGGAAGGCGATAAGGTTAA 3' |
| | PD-9 | 45 | 5' TTATCGATTGACGTTACCCGCAGAAGA 3' |
| | PD-10 | 46 | 5' CATTCGAAACTGGCAGGCTAGAGTC 3' |
| | PD-11 | 47 | 5' CCTTTGTTGCCAGCGGTTAGGC 3' |

TABLE 5

Probes for detecting *Pseudomonas aeruginosa* strain

| Name of microorganizm | Probe No. | SEQ ID No. | Sequence |
|---|---|---|---|
| *Pseudomonas aeruginosa* | PE-1 | 48 | 5' TGAGGGAGAAAGTGGGGGATCTTC 3' |
| | PE-2 | 49 | 5' TCAGATGAGCCTAGGTCGGATTAGC 3' |
| | PE-3 | 50 | 5' GAGCTAGAGTACGGTAGAGGGTGG 3' |
| | PE-4 | 51 | 5' GTACGGTAGAGGGTGGTGGAATTT 3' |
| | PE-5 | 52 | 5' GACCACCTGGACTGATACTGACAC 3' |
| | PE-6 | 53 | 5' TGGCCTTGACATGCTGAGAACTTTC 3' |
| | PE-7 | 54 | 5' TTAGTTACCAGCACCTCGGGTGG 3' |
| | PE-8 | 55 | 5' TAGTCTAACCGCAAGGGGACG 3' |
| | PE-9 | 56 | 5' TGCATCCAAAACTACTGAGCTAGAGTAC 3' |
| | PE-10 | 57 | 5' GTCGACTAGCCGTTGGGATCCT 3' |

TABLE 6

Probes for detecting *Serratia marcescens* strain

| Name of microorganizm | Probe No. | SEQ ID No. | Sequence |
|---|---|---|---|
| *Serratia marcescens* | PF-1 | 58 | 5' TAGCACAGGGAGCTTGCTCCCT 3' |
| | PF-2 | 59 | 5' AGGTGGTGAGCTTAATACGCTCATC 3' |
| | PF-3 | 60 | 5' TCATCAATTGACGTTACTCGCAGAAG 3' |
| | PF-4 | 61 | 5' ACTGCATTTGAAACTGGCAAGCTAGA 3' |
| | PF-5 | 62 | 5' TTATCCTTTGTTGCAGCTTCGGCC 3' |
| | PF-6 | 63 | 5' ACTTTCAGCGAGGAGGAAGGTGG 3' |

TABLE 6-continued

Probes for detecting *Serratia marcescens* strain

| Name of microorganizm | Probe No. | SEQ ID No. | Sequence |
|---|---|---|---|
| | PF-7 | 64 | 5' GGTAGCACAGGGGAGCTTGCTC 3' |
| | PF-8 | 65 | 5' CGAGGAGGAAGGTGGTGAGCTTAATA 3' |
| | PF-9 | 66 | 5' TACGCTCATCAATTGACGTTACTCGC 3' |
| | PF-10 | 67 | 5' GAAACTGGCAAGCTAGAGTCTCGTAGA 3' |
| | PF-11 | 68 | 5' TTATCCTTTGTTGCCAGCGGTTCG 3' |

TABLE 7

Probes for detecting *Streptococcus pneumoniae* strain

| Name of microorganizm | Probe No. | SEQ ID No. | Sequence |
|---|---|---|---|
| *Streptococcus pneumoniae* | PG-1 | 69 | 5' AGTAGAACGCTGAAGGAGGAGCTTG 3' |
| | PG-2 | 70 | 5' CTTGCATCACTACCAGATGGACCTG 3' |
| | PG-3 | 71 | 5' TGAGAGTGGAAAGTTCACACTGTGAC 3' |
| | PG-4 | 72 | 5' GCTGTGGCTTAACCATAGTAGGCTTT 3' |
| | PG-5 | 73 | 5' AAGCGGCTCTCTGGCTTGTAACT 3' |
| | PG-6 | 74 | 5' TAGACCCTTTCCGGGGTTTAGTGC 3' |
| | PG-7 | 75 | 5' GACGGCAAGCTAATCTCTTAAAGCCA 3' |
| | PG-8 | 76 | 5' GACATTTGCTTAAAAGGTGCACTTGCA 3' |
| | PG-9 | 77 | 5' GTTGTAAGAGAAGAACGAGTGTGAGAGTG 3' |

TABLE 8

Probes for detecting *Haemophilus influenzae* strain

| Name of microorganizm | Probe No. | SEQ ID No. | Sequence |
|---|---|---|---|
| *Haemophilus influenzae* | PH-1 | 78 | 5' GCTTGGGAATCTGGCTTATGGAGG 3' |
| | PH-2 | 79 | 5' TGCCATAGGATGAGCCCAAGTGG 3' |
| | PH-3 | 80 | 5' CTTGGGAATGTACTGACGCTCATGTG 3' |
| | PH-4 | 81 | 5' GGATTGGGCTTAGAGCTTGGTGC 3' |
| | PH-5 | 82 | 5' TACAGAGGGAAGCGAAGCTGCG 3' |
| | PH-6 | 83 | 5' GGCGTTTACCACGGTATGATTCATGA 3' |
| | PH-7 | 84 | 5' AATGCCTACCAAGCCTGCGATCT 3' |
| | PH-8 | 85 | 5' TATCGGAAGATGAAAGTGCGGGACT 3' |

TABLE 9

Probes for detecting *Enterobacter Cloacae* strain

| Name of microorganizm | Probe No. | SEQ ID No. | Sequence |
|---|---|---|---|
| *Enterobacter Cloacae* | PI-1 | 86 | 5' CAGAGAGCTTGCTCTCGGGTGA 3' |
| | PI-2 | 87 | 5' GGGAGGAAGGTGTTGTGGTTAATAAC 3' |
| | PI-3 | 88 | 5' GGTGTTGTGGTTAATAACCACAGCAA 3' |
| | PI-4 | 89 | 5' GCGGTCTGTCAAGTCGGATGTG 3' |
| | PI-5 | 90 | 5' ATTCGAAACTGGCAGGCTAGAGTCT 3' |
| | PI-6 | 91 | 5' TAACCACAGCAATTGACGTTACCCG 3' |
| | PI-7 | 92 | 5' GCAATTGACGTTACCCGCAGAAGA 3' |
| | PI-8 | 93 | 5' GTAGCACAGAGAGCTTGCTCTCG 3' |
| | PI-9 | 94 | 5' CGGGGAGGAAGGTGTTGTGGTTA 3' |
| | PI-10 | 95 | 5' ACCACAGCAATTGACGTTACCCG 3' |
| | PI-11 | 96 | 5' GAAACTGGCAGGCTAGAGTCTTGTAG 3' |
| | PI-12 | 97 | 5' AGGCGGTCTGTCAAGTCGGATG 3' |

TABLE 10

Probes for detecting *Enterococcus faecalis* strain

| Name of microorganizm | Probe No. | SEQ ID No. | Sequence |
|---|---|---|---|
| *Enterococcus faecalis* | PJ-1 | 98 | 5' TTCTTTCCTCCCGAGTGCTTGCA 3' |
| | PJ-2 | 99 | 5' AACACGTGGGTAACCTACCCATCAG 3' |
| | PJ-3 | 100 | 5' ATGGCATAAGAGTGAAAGGCGCTT 3' |
| | PJ-4 | 101 | 5' GACCCGCGGTGCATTAGCTAGT 3' |
| | PJ-5 | 102 | 5' GGACGTTAGTAACTGAACGTCCCCT 3' |
| | PJ-6 | 103 | 5' CTCAACCGGGGAGGGTCATTGG 3' |
| | PJ-7 | 104 | 5' TTGGAGGGTTTCCGCCCTTCAG 3' |
| | PJ-8 | 105 | 5' ATAGAGCTTTCCCTTCGGGGACAAA 3' |
| | PJ-9 | 106 | 5' CGAGGTCATGCAAATCTCTTAAAGCTTCT 3' |

For each probe shown in the tables, as a functional group to immobilize the probe to a DNA microarray, a thiol group was introduced to the 5' terminal of the nucleic acid after synthesis in accordance with a conventional method. After introduction of the functional group, purification and freeze-drying were executed. The freeze-dried probes were stored in a freezer at −30° C.

2. Preparation of Specimen Amplification PCR Primers

As 16s rRNA gene (target gene) amplification PCR primers for etiologic agent detection, nucleic acid sequences shown in Table 11 were designed. More specifically, probe sets which specifically amplify the genome parts coding the 16s rRNAs, i.e., primers for which the specific melting points were made uniform as much as possible at the two end portions of the 16s rRNA coding region of a base length of 1,400 to 1,700 were designed. In order to simultaneously amplify variants or a plurality of 16s rRNA coding regions on genomes, a plurality of kinds of primers were designed. Note that a primer set is not limited to primer sets shown in the table 11. A primer set which is available in common to a plural kinds of etiologic agents and amplify almost entire length of 16s rRNA coding region of the etiologic agents can also be employed.

TABLE 11

| Primer | Primer No. | SEQ ID No. | Sequence |
|---|---|---|---|
| Forward Primer | F-1 | 107 | 5' GCGGCGTGCCTAATACATGCAAG 3' |
|  | F-2 | 108 | 5' GCGGCAGGCCTAACACATGCAAG 3' |
|  | F-3 | 109 | 5' GCGGCAGGCTTAACACATGCAAG 3' |
| Reverse Primer | R-1 | 110 | 5' ATCCAGCCGCACCTTCCGATAC 3' |
|  | R-2 | 111 | 5' ATCCAACCGCAGGTTCCCCTAC 3' |
|  | R-3 | 112 | 5' ATCCAGCCGCAGGTTCCCCTAC 3' |

The primers shown in Table 11 were purified by HPLC (High Performance Liquid Chromatography) after synthesis. Three forward primers and three reverse primers were mixed and dissolved in a TE buffer solution such that each primer concentration had an ultimate concentration of 10 pmol/μl.

3. Extraction of Genome DNAs (Model Specimens) of Etiologic Agents

[3-1] Microbial Culture & Preprocess for Genome DNA Extraction

First, microbial culture media were produced by culturing type strains of the etiologic agents (*Staphylococcus aureus* type strain (ATCC12600), *Staphylococcus epidermidis* type strain (ATCC14990), *Escherichia coli* type strain (ATCC11775), *Klebsiella pneumoniae* type strain (ATCC13883), *Pseudomonas aeruginosa* type strain (ATCC10145), *Serratia marcescens* strain, *Streptococcus pneumoniae* type strain, *Haemophilus influenzae*strain, *Enterobacter Cloacae* type strain (ATCC13047), and *Enterococcus faecalis* type strain (ATCC19433)) in accordance with a conventional method. Each of the microbial culture media was sampled 1.0 ml ($OD_{600}$=0.7) into a 1.5-ml microtube. The cells were collected by centrifuge (8,500 rpm, 5 min, 4° C.). After the supernatant was removed, a 300-μl enzyme buffer (50 mM Tris-HCl: p.H. 8.0, 25 mM EDTA) was added, and the broth was re-suspended by using a mixer. From the re-suspended broth, the cells were collected again by centrifuge (8,500 rpm, 5 min, 4° C.). After the supernatant was removed, the following enzyme solution was added to the collected cells, and the broth was re-suspended by using the mixer.

Lysozyme 50 μl (20 mg/ml in Enzyme Buffer)

N-Acetylmuramidase SG 50 μl (0.2 mg/ml in Enzyme Buffer)

The broth added with the enzyme solution and re-suspended was left stand still in an incubator at 37° C. for 30 min to melt cell walls.

[3-2] Genome Extraction

Microbial genome DNA extraction to be described below was done by using a nucleic acid purification kit (MagExtractor-Genome: available from TOYOBO).

More specifically, a 750-μl melting/absorption solution and a 40-μl magnetic beads were added to the preprocessed microbial suspension. The suspension was intensely stirred for 10 min by using a tube mixer (step 1).

Next, the microtube was set in a separation stand (Magical Trapper) and left stand still for 30 sec to gather magnetic particles to the wall surface of the tube. The supernatant was removed while the microtube was kept set in the stand (step 2).

Next, a 900-μl cleaning solution was added. The solution was re-suspended by stirring it for about 5 sec by a mixer (step 3).

The microtube was set in the separation stand (Magical Trapper) and left stand still for 30 sec to gather magnetic particles to the wall surface of the tube. The supernatant was removed while the microtube was kept set in the stand (step 4).

Steps 3 and 4 were repeated to execute the second cleaning process (step 5). After that, 900-μl 70% ethanol was added. The solution was re-suspended by stirring it for about 5 sec by a mixer (step 6).

The microtube was set in the separation stand (Magical Trapper) and left stand still for 30 sec to gather magnetic particles to the wall surface of the tube. The supernatant was removed while the microtube was kept set in the stand (step 7).

Steps 6 and 7 were repeated to execute the second cleaning process by using 70% ethanol (step 8). After that, 100-μl pure water was added to the collected magnetic particles. The solution was stirred for 10 min by a tube mixer (step 9).

The microtube was set in the separation stand (Magical Trapper) and left stand still for 30 sec to gather magnetic particles to the wall surface of the tube. The supernatant was collected to a new tube while the microtube was kept set in the stand.

[3-3] Test of Collected Genome DNAs

The collected genome DNAs of microorganisms (etiologic agent strain) underwent agarose electrophoresis and 260/280-nm absorbance determination in accordance with the conventional method so that the quality (the admixture amount of low molecular nucleic acid and the degree of decomposition) and collection amount were tested. In this embodiment, about 9 to 10-μg genome DNAs were collected in each bacterium. No degradation of genome DNAs or admixture of rRNA was observed. The collected genome DNAs were dissolved in a TE buffer solution at an ultimate concentration of 50 ng/μl and used in the following examples.

4. Preparation of DNA Microarray

The DNA Microarray was prepared according to Japanese Patent Application Laid-Open No. 11-187900.

[4-1] Cleaning of Glass Substrate

A glass substrate (size: 25 mm×75 mm×1 mm, available from Iiyama Tokushu Glass) made of synthetic silica was placed in a heat- and alkali-resisting rack and dipped in a cleaning solution for ultrasonic cleaning, which was prepared to a predetermined concentration. The glass substrate was kept dipped in the cleaning solution for a night and cleaned by ultrasonic cleaning for 20 min. The substrate was picked up, lightly rinsed by pure water, and cleaned by ultrasonic cleaning in ultrapure water for 20 min. The substrate was dipped in a 1N aqueous sodium hydroxide solution heated to 80° C. for 10 min. Pure water cleaning and ultrapure water cleaning were executed again. A silica glass substrate for a DNA microchip was thus prepared.

[4-2] Surface Treatment

A silane coupling agent KBM-603 (available from Shinetsu Silicone) was dissolved in pure water at a concentration of 1% and stirred at room temperature for 2 hrs. The cleaned glass substrate was dipped in the aqueous solution of the silane coupling agent and left stand still at room temperature for 20 min. The glass substrate was picked up. The surface was lightly rinsed by pure water and dried by spraying nitrogen gas to both surfaces of the substrate. The dried substrate was baked in an oven at 120° C. for 1 hr to complete the coupling agent treatment, thereby introducing an amino group to the substrate surface. Next, N-(6-Maleimidocaproyloxy)succinimido) (to be abbreviated as EMCS hereinafter) available from Dojindo Laboratories was dissolved in a 1:1 medium mixture of dimethyl sulfoxide and ethanol such that an ultimate concentration of 0.3 mg/ml was obtained, thereby preparing an EMCS solution.

The baked glass substrate was left stand and cooled and dipped in the prepared EMCS solution at room temperature for 2 hrs. With this process, the amino group introduced to the surface by the silane coupling agent reacted with the succinimide group in the EMCS to introduce the maleimide group to the surface of the glass substrate. The glass substrate picked up from the EMCS solution was cleaned by using the above-described medium mixture in which the EMCS was dissolved. The glass substrate was further cleaned by ethanol and dried in a nitrogen gas atmosphere.

[4-3] Probe DNA

The microorganism detection probe prepared in Example 1 was dissolved in pure water. The solution was dispensed such that the ultimate concentration (at ink dissolution) became 10 µM. Then, the solution was freeze-dried to remove water.

[4-4] DNA Discharge by BJ Printer and Bonding to Substrate

An aqueous solution containing 7.5-wt % glycerin, 7.5-wt % thioglycol, 7.5-wt % urea, and 1.0-wt % Acetylenol EH (available from Kawaken Fine Chemicals) was prepared. Each of the seven probes (Table 1) prepared in advance was dissolved in the medium mixture at a specific concentration. An ink tank for an inkjet printer (tradename: BJF-850, available from Canon) is filled with the resultant DNA solution and attached to the printhead.

The inkjet printer used here was modified in advance to allow printing on a flat plate. When the inkjet printer inputs a printing pattern in accordance with a predetermined file creation method, an about 5-picoliter DNA solution can be spotted at a pitch of about 120 µm.

The printing operation was executed for one glass substrate by using the modified inkjet printer, thereby preparing a DNA microarray. After confirming that printing was reliably executed, the glass substrate was left stand still in a humidified chamber for 30 min to make the maleimide group on the glass substrate surface react with the thiol group at the nucleic acid probe terminal.

[4-5] Cleaning

After reaction for 30 min, the DNA solution remaining on the surface was cleaned by using a 10-mM phosphate buffer (pH 7.0) containing 100-mM NaCl, thereby obtaining a gene chip (DNA microarray) in which single-stranded DNAs were immobilized on the glass substrate surface.

5. Amplification and Labeling of Specimens (PCR Amplification & Fluorescent Labeling)

Amplification of microbial genes as specimens and labeling reaction will be described below

| Premix PCR reagent (TAKARA ExTaq) | 25 µl | |
| Template Genome DNA | 2 µl | (100 ng) |
| Forward Primer mix | 2 µl | (20 pmol/tube each) |
| Reverse Primer mix | 2 µl | (20 pmol/tube each) |
| Cy-3 dUTP (1 mM) | 2 µl | (2 nmol/tube) |
| $H_2O$ | 17 µl | |
| Total | 50 µl | |

Amplification reaction of the reaction solution having the above composition was caused by using a commercially available thermal cycler in accordance with the following protocol.

| 95° C. | 10 min. | |
| 92° C. | 45 sec. | 35 Cycles |
| 55° C. | 45 sec. | |
| 72° C. | 45 sec. | |
| 72° C. | 10 min. | |

After the end of reaction, the primers were removed (purified) by using a purification column (QIAquick PCR Purification Kit available from QIAGEN). Then, determination of the amplified products was executed to obtain labeled specimens.

6. Hybridization

Detection reaction was performed by using the gene chips prepared by [4. Preparation of DNA Microarray] and the labeled specimen prepared by [5. Amplification and Labeling of Specimen (PCR Amplification & Fluorescent Labeling)].

[6-1] Blocking of DNA Microarrays

BSA (fetal bovine serum albumin, Fraction V: available from Sigma) was dissolved in a 100-mM NaCl/10-mM phosphate buffer such that a 1 wt % solution was obtained. The gene chips prepared by [4. Preparation of DNA Microarray] were dipped in the solution at room temperature for 2 hrs to execute blocking. After the end of blocking, the chips were cleaned by using a 2×SSC solution (NaCl 300 mM, Sodium Citrate (trisodium citrate dihydrate, $C_6H_5Na_3.2H_2O$) 30 mM, pH 7.0) containing 0.1-wt % SDS (Sodium Dodecyl Sulfate), rinsed by pure water, and hydro-extracted by a spin dryer.

[6-2] Hybridization

The hydro-extracted gene chips were set in a hybridization apparatus (Hybridization Station available from Genomic Solutions Inc). Hybridization reaction was caused in a hybridization solution under conditions to be described below.

[6-3] Hybridization Solution

6×SSPE/10% Form amide/Target (all 2nd PCR Products)
6×SSPE: NaCl 900 mM, NaH$_2$PO$_4$.H$_2$O 60 mM, EDTA 6 mM, pH, 7.4)

[6-4] Hybridization Conditions

65° C. 3 min →92° C. 2 min →45° C. 3 hrs →Wash 2×SSC/0.1% SDS at 25° C. →Wash 2×SSC at 20° C. →(Rinse with H$_2$O: Manual) →Spin dry (The hybridization reaction was caused at 65° C. for 3 min, at 92° C. for 2 min, and at 45° C. for 3 hrs. The gene chips were cleaned by using 2×SSC/0.1% SDS at 25° C. and 2×SSC at 20° C., rinsed by pure water, and spin-dried).

7. Microorganism Detection (Fluorometry)

The gene chips after the end of hybridization reaction were subjected to fluorometry by using a gene chip fluorescent detector (GenePix 4000B available from Axon). As a result, the respective bacteria could be detected with sufficient signals at a high reproducibility, as shown in Tables 12 to 21. No hybrid bodies for other bacteria were detected.

In this example, fluorometry was executed twice for each gene chip. The results are shown below.

TABLE 12

*Staphylococcus aureus*

| Probe No. | SEQ. ID. No. | Sequence | First Fluorescence luminance | S/N | Second Fluorescence luminance | S/N |
|---|---|---|---|---|---|---|
| PA-1 | 1 | 5' GAACCGCATGGTTCAAAAGTGAAAGA 3' | 3000 | 42.9 | 2900 | 40.8 |
| PA-2 | 2 | 5' CACTTATAGATGGATCCGCGCTGC 3' | 7700 | 110.0 | 7700 | 108.5 |
| PA-3 | 3 | 5' TGCACATCTTGACGGTACCTAATCAG 3' | 6400 | 91.4 | 6400 | 90.1 |
| PA-4 | 4 | 5' CCCCTTAGTGCTGCAGCTAACG 3' | 2500 | 35.7 | 2500 | 35.2 |
| PA-5 | 5 | 5' AATACAAAGGGCAGCGAAACCGC 3' | 7800 | 111.4 | 7800 | 109.9 |
| PA-6 | 6 | 5' CCGGTGGAGTAACCTTTTAGGAGCT 3' | 4800 | 68.6 | 4800 | 67.6 |
| PA-7 | 7 | 5' TAACCTTTTAGGAGCTAGCCGTCGA 3' | 4500 | 64.3 | 4300 | 60.6 |
| PA-8 | 8 | 5' TTTAGGAGCTAGCCGTCGAAGGT 3' | 4800 | 68.6 | 4800 | 67.6 |
| PA-9 | 9 | 5' TAGCCGTCGAAGGTGGGACAAAT 3' | 5300 | 75.7 | 5200 | 73.2 |

TABLE 13

*Staphylococcus epidermidis*

| Probe No. | SEQ. ID. No. | Sequence | First Fluorescence luminance | S/N | Second Fluorescence luminance | S/N |
|---|---|---|---|---|---|---|
| PB-1 | 15 | 5' GAACAGACGAGGAGCTTGCTCC 3' | 1000 | 14.5 | 1100 | 15.7 |
| PB-2 | 16 | 5' TAGTGAAAGACGGTTTTGCTGTCACT 3' | 1800 | 26.1 | 1800 | 25.7 |
| PB-3 | 17 | 5' TAAGTAACTATGCACGTCTTGACGGT 3' | 1400 | 20.3 | 1400 | 20 |
| PB-4 | 18 | 5' GACCCCTCTAGAGATAGAGTTTTCCC 3' | 1000 | 14.5 | 1100 | 15.7 |
| PB-5 | 19 | 5' AGTAACCATTTGGAGCTAGCCGTC 3' | 1800 | 26.1 | 2000 | 28.6 |
| PB-6 | 20 | 5' GAGCTTGCTCCTCTGACGTTAGC 3' | 1200 | 17.4 | 1300 | 18.6 |
| PB-7 | 21 | 5' AGCCGGTGGAGTAACCATTTGG 3' | 1100 | 15.9 | 1100 | 15.7 |

TABLE 14

Escherichia coli

| Probe No. | SEQ. ID. No. | Sequence | First Fluorescence luminance | S/N | Second Fluorescence luminance | S/N |
|---|---|---|---|---|---|---|
| PC-1 | 25 | 5' CTCTTGCCATCGGATGTGCCCA 3' | 1200 | 17.6 | 1200 | 17.9 |
| PC-2 | 26 | 5' ATACCTTTGCTCATTGACGTTACCCG 3' | 1500 | 22.1 | 1600 | 23.9 |
| PC-3 | 27 | 5' TTTGCTCATTGACGTTACCCGCAG 3' | 1100 | 16.2 | 1200 | 17.9 |
| PC-4 | 28 | 5' ACTGGCAAGCTTGAGTCTCGTAGA 3' | 2000 | 29.4 | 2100 | 31.3 |
| PC-5 | 29 | 5' ATACAAAGAGAAGCGACCTCGCG 3' | 1500 | 22.1 | 1500 | 22.4 |
| PC-6 | 30 | 5' CGGACCTCATAAAGTGCGTCGTAGT 3' | 2400 | 35.3 | 2600 | 38.8 |
| PC-7 | 31 | 5' GCGGGGAGGAAGGGAGTAAAGTTAAT 3' | 1200 | 17.6 | 1200 | 17.9 |

TABLE 15

Klebsiella pneumoniae

| Probe No. | SEQ. ID. No. | Sequence | First Fluorescence luminance | S/N | Second Fluorescence luminance | S/N |
|---|---|---|---|---|---|---|
| PD-1 | 37 | 5' TAGCACAGAGAGCTTGCTCTCGG 3' | 500 | 7.6 | 600 | 9 |
| PD-2 | 38 | 5' TCATGCCATCAGATGTGCCCAGA 3' | 600 | 9.1 | 600 | 9 |
| PD-3 | 39 | 5' CGGGGAGGAAGGCGATAAGGTTAAT 3' | 700 | 10.6 | 700 | 10.4 |
| PD-4 | 40 | 5' TTCGATTGACGTTACCCGCAGAAGA 3' | 1000 | 15.2 | 1200 | 17.9 |
| PD-5 | 41 | 5' GGTCTGTCAAGTCGGATGTGAAATCC 3' | 2700 | 40.9 | 2700 | 40.3 |
| PD-6 | 42 | 5' GCAGGCTAGAGTCTTGTAGAGGGG 3' | 3400 | 51.5 | 3300 | 49.3 |

TABLE 16

Pseudomonas aeruginosa

| Probe No. | SEQ. ID. No. | Sequence | First Fluorescence luminance | S/N | Second Fluorescence luminance | S/N |
|---|---|---|---|---|---|---|
| PE-1 | 48 | 5' TGAGGGAGAAAGTGGGGGATCTTC 3' | 3500 | 50.0 | 3600 | 50 |
| PE-2 | 49 | 5' TCAGATGAGCCTAGGTCGGATTAGC 3' | 1600 | 22.9 | 1400 | 19.4 |
| PE-3 | 50 | 5' GAGCTAGAGTACGGTAGAGGGTGG 3' | 3500 | 50.0 | 3400 | 47.2 |
| PE-4 | 51 | 5' GTACGGTAGAGGGTGGTGGAATTT 3' | 3100 | 44.3 | 3100 | 43.1 |
| PE-5 | 52 | 5' GACCACCTGGACTGATACTGACAC 3' | 1600 | 22.9 | 1600 | 22.2 |
| PE-6 | 53 | 5' TGGCCTTGACATGCTGAGAACTTTC 3' | 1200 | 17.1 | 1200 | 16.7 |
| PE-7 | 54 | 5' TTAGTTACCAGCACCTCGGGTGG 3' | 1000 | 14.3 | 1200 | 16.7 |
| PE-8 | 55 | 5' TAGTCTAACCGCAAGGGGGACG 3' | 1100 | 15.7 | 1100 | 15.3 |

TABLE 17

| | | | First | | Second | |
|---|---|---|---|---|---|---|
| Probe No. | SEQ. ID. No. | Sequence | Fluorescence luminance | S/N | Fluorescence luminance | S/N |
| | | *Serratia marcescens* | | | | |
| PF-1 | 58 | 5' TAGCACAGGGAGCTTGCTCCCT 3' | 600 | 8.8 | 600 | 8.7 |
| PF-2 | 59 | 5' AGGTGGTGAGCTTAATACGCTCATC 3' | 700 | 10.3 | 600 | 8.7 |
| PF-3 | 60 | 5' TCATCAATTGACGTTACTCGCAGAAG 3' | 2000 | 29.4 | 2200 | 31.9 |
| PF-4 | 61 | 5' ACTGCATTTGAAACTGGCAAGCTAGA 3' | 2800 | 41.2 | 2700 | 39.1 |
| PF-5 | 62 | 5' TTATCCTTTGTTGCAGCTTCGGCC 3' | 700 | 10.3 | 700 | 10.1 |
| PF-6 | 63 | 5' ACTTTCAGCGAGGAGGAAGGTGG 3' | 3400 | 50.0 | 3300 | 47.8 |

TABLE 18

| | | | First | | Second | |
|---|---|---|---|---|---|---|
| Probe No. | SEQ. ID. No. | Sequence | Fluorescence luminance | S/N | Fluorescence luminance | S/N |
| | | *Streptococcus pneumoniae* | | | | |
| PG-1 | 69 | 5' AGTAGAACGCTGAAGGAGGAGCTTG 3' | 1000 | 14.9 | 1100 | 16.2 |
| PG-2 | 70 | 5' CTTGCATCACTACCAGATGGACCTG 3' | 1200 | 17.9 | 1300 | 19.1 |
| PG-3 | 71 | 5' TGAGAGTGGAAAGTTCACACTGTGAC 3' | 1000 | 14.9 | 1100 | 16.2 |
| PG-4 | 72 | 5' GCTGTGGCTTAACCATAGTAGGCTTT 3' | 1800 | 26.9 | 1900 | 27.9 |
| PG-5 | 73 | 5' AAGCGGCTCTCTGGCTTGTAACT 3' | 1300 | 19.4 | 1500 | 22.1 |
| PG-6 | 74 | 5' TAGACCCTTTCCGGGGTTTAGTGC 3' | 1300 | 19.4 | 1300 | 19.1 |
| PG-7 | 75 | 5' GACGGCAAGCTAATCTCTTAAAGCCA 3' | 2000 | 29.9 | 2100 | 30.9 |

TABLE 19

| | | | First | | Second | |
|---|---|---|---|---|---|---|
| Probe No. | SEQ. ID. No. | Sequence | Fluorescence luminance | S/N | Fluorescence luminance | S/N |
| | | *Haemophilus influenzae* | | | | |
| PH-1 | 78 | 5' GCTTGGGAATCTGGCTTATGGAGG 3' | 3500 | 50.0 | 3600 | 50 |
| PH-2 | 79 | 5' TGCCATAGGATGAGCCCAAGTGG 3' | 600 | 8.8 | 700 | 10.1 |
| PH-3 | 80 | 5' CTTGGGAATGTACTGACGCTCATGTG 3' | 600 | 8.8 | 600 | 8.7 |
| PH-4 | 81 | 5' GGATTGGGCTTAGAGCTTGGTGC 3' | 1100 | 16.2 | 1200 | 17.4 |
| PH-5 | 82 | 5' TACAGAGGGAAGCGAAGCTGCG 3' | 700 | 10.3 | 600 | 8.7 |
| PH-6 | 83 | 5' GGCGTTTACCACGGTATGATTCATGA 3' | 1300 | 19.1 | 1300 | 18.8 |
| PH-7 | 84 | 5' AATGCCTACCAAGCCTGCGATCT 3' | 2100 | 30.9 | 2200 | 31.9 |
| PH-8 | 85 | 5' TATCGGAAGATGAAAGTGCGGGACT 3' | 700 | 10.3 | 600 | 8.7 |

TABLE 20

Enterobacter cloacae

| Probe No. | SEQ. ID. No. | Sequence | First Fluorescence luminance | S/N | Second Fluorescence luminance | S/N |
|---|---|---|---|---|---|---|
| PI-1 | 86 | 5' CAGAGAGCTTGCTCTCGGGTGA 3' | 2100 | 29.2 | 2200 | .31 |
| PI-2 | 87 | 5' GGGAGGAAGGTGTTGTGGTTAATAAC 3' | 7900 | 109.7 | 7900 | 111.3 |
| PI-3 | 88 | 5' GGTGTTGTGGTTAATAACCACAGCAA 3' | 1000 | 13.9 | 1300 | 18.3 |
| PI-4 | 89 | 5' GCGGTCTGTCAAGTCGGATGTG 3' | 6400 | 88.9 | 6400 | 90.1 |
| PI-5 | 90 | 5' ATTCGAAACTGGCAGGCTAGAGTCT 3' | 9400 | 130.6 | 9200 | 129.6 |
| PI-6 | 91 | 5' TAACCACAGCAATTGACGTTACCCG 3' | 4700 | 65.3 | 4800 | 67.6 |
| PI-7 | 92 | 5' GCAATTGACGTTACCCGCAGAAGA 3' | 4600 | 63.9 | 4500 | 63.6 |

TABLE 21

Enterococcus faecalis

| Probe No. | SEQ. ID. No. | Sequence | First Fluorescence luminance | S/N | Second Fluorescence luminance | S/N |
|---|---|---|---|---|---|---|
| PJ-1 | 98 | 5'TTCTTTCCTCCCGAGTGCTTGCA 3' | 1500 | 22.1 | 1500 | 20.8 |
| PJ-2 | 99 | 5'AACACGTGGGTAACCTACCCATCAG 3' | 2400 | 35.3 | 2700 | 37.5 |
| PJ-3 | 100 | 5'ATGGCATAAGAGTGAAAGGCGCGTT 3' | 5600 | 82.4 | 5600 | 77.8 |
| PJ-4 | 101 | 5'GACCCGCGGTGCATTAGCTAGT 3' | 2300 | 33.8 | 2300 | 31.9 |
| PJ-5 | 102 | 5'GGACGTTAGTAACTGAACGTCCCCT 3' | 1000 | 14.7 | 1400 | 19.4 |
| PJ-6 | 103 | 5'CTCAACCGGGGAGGGTCATTGG 3' | 4400 | 64.7 | 4400 | 61.1 |
| PJ-7 | 104 | 5'TTGGAGGGTTTCCGCCCTTCAG 3' | 1700 | 25 | 1800 | 25 |

The numerical values of florescent luminances (photomultiplier voltage: 400 V) in Tables 12 to 21 indicate average pixel luminances (resolution: 5 μm). The S/N ratios indicate values obtained by dividing the fluorescent luminances by background average values measured by analysis software (GenePix Pro Ver.3.0 available from Axon) attached to the measuring device.

As is apparent from Tables 12 to 21, the respective etiologic agents can be detected with sufficient signals at a high reproducibility.

Example 2

Microorganism Detection Using 2-Step PCR

As in Example 1, probe DNAs, specimen amplification PCR primers, the genome DNAs of etiologic agents, and DNA microarrays were prepared, and the following experiments were conducted.

1. Amplification and Labeling of Specimens (PCR Amplification & Fluorescent Labeling)

Amplification of microbial genes as specimens (1st PCR) and labeling (2nd PCR) reaction will be described below.

2. Amplification Reaction Solution Composition: 1st PCR

Premix PCR reagent (TAKARA 25 μl ExTaq)

| | | |
|---|---|---|
| Template Genome DNA | 2 μl | (10 ng) |
| Forward Primer mix | 2 μl | (20 pmol/tube each) |
| Reverse Primer mix | 2 μl | (20 pmol/tube each) |
| H₂0 | 19 μl | |
| Total | 50 μl | |

Amplification reaction of the reaction solution having the above composition was caused by using a commercially available thermal cycler in accordance with the following protocol.

| | |
|---|---|
| 95° C. | 10 min. |
| 92° C. | 45 sec. |
| 55° C. | 45 sec. } 25 Cycles |
| 72° C. | 45 sec. |
| 72° C. | 10 min. |

After the end of reaction, purification was performed by using a purification column (QIAquick PCR Purification Kit available from QIAGEN). Then, determination of the amplified products was executed.

3. Labeling Reaction Solution Composition: 2nd PCR Enzyme

| | | |
|---|---|---|
| (QIAGEN Hotstar Taq Polymerase) | 0.5 μl | (2.5 u) |
| Template DNA (1st PCR Product) | 10 μl | (30 ng) |
| dNTP mix (Low dTTP)* | 2 μl | |
| Cy-3 dUTP (1 mM) | 2 μl | (2 nmol/tube) |
| Reverse Primer mix | 5 μl | (50 pmol/tube each) |
| 10 × Buffer | 5 μl | |
| H₂0 | 25.5 μl | |
| Total | 50 μl | |

*dNTP mix (Low dTTP): dATP, dCTP, dGTP/5 mM(final: 10 nmol/tube) dTTP/4 mM (final: 8 nmol/tube)

Amplification reaction of the reaction solution having the above composition was caused by using a commercially available thermal cycler in accordance with the following protocol.

| | |
|---|---|
| 95° C. | 10 min. |
| 92° C. | 45 sec. |
| 55° C. | 45 sec. } 25 Cycles |
| 72° C. | 45 sec. |
| 72° C. | 10 min. |

After the end of reaction, purification was performed by using a purification column (QIAquick PCR Purification Kit available from QIAGEN) to obtain labeled specimens.

4. Hybridization

Hybridization was done in accordance with the same procedures as in Example 1.

5. Microorganism Detection (Fluorometry)

Fluorometry was executed for the DNA microarrays after the end of hybridization reaction by using a DNA microarray fluorescent detector (GenePix 4000B available from Axon). Tables 22 to 31 show the measurement results.

Even in this example, fluorometry was executed twice for each DNA microarray. The results are shown in Tables 22 to 31.

TABLE 22

*Staphylococcus aureus*

| | | | First | | Second | |
|---|---|---|---|---|---|---|
| Probe No. | SEQ. ID. No. | Sequence | Fluorescence luminance | S/N | Fluorescence luminance | S/N |
| PA-1 | 1 | 5' GAACCGCATGGTTCAAAAGTGAAAGA 3' | 14000 | 186.7 | 13000 | 173.3 |
| PA-2 | 2 | 5' CACTTATAGATGGATCCGCGCTGC 3' | 36000 | 480 | 35000 | 466.7 |
| PA-3 | 3 | 5' TGCACATCTTGACGGTACCTAATCAG 3' | 31000 | 413.3 | 29000 | 386.7 |
| PA-4 | 4 | 5' CCCCTTAGTGCTGCAGCTAACG 3' | 10000 | 133.3 | 10000 | 133.3 |
| PA-5 | 5 | 5' AATACAAAGGGCAGCGAAACCGC 3' | 39000 | 520 | 38500 | 513.3 |
| PA-6 | 6 | 5' CCGGTGGAGTAACCTTTTAGGAGCT 3' | 22000 | 293.3 | 22100 | 294.7 |
| PA-7 | 7 | 5' TAACCTTTTAGGAGCTAGCCGTCGA 3' | 22000 | 293.3 | 21800 | 290.7 |
| PA-8 | 8 | 5' TTTAGGAGCTAGCCGTCGAAGGT 3' | 25000 | 333.3 | 24000 | 320 |
| PA-9 | 9 | 5' TAGCCGTCGAAGGTGGGACAAAT 3' | 26000 | 346.7 | 25500 | 340 |

TABLE 23

*Staphylococcus epidermidis*

| | | | First | | Second | |
|---|---|---|---|---|---|---|
| Probe No. | SEQ. ID. No. | Sequence | Fluorescence luminance | S/N | Fluorescence luminance | S/N |
| PB-1 | 15 | 5' GAACAGACGAGGAGCTTGCTCC 3' | 4500 | 62.5 | 4700 | 67.1 |
| PB-2 | 16 | 5' TAGTGAAAGACGGTTTTGCTGTCACT 3' | 9000 | 125 | 8900 | 127.1 |

TABLE 23-continued

*Staphylococcus epidermidis*

| Probe No. | SEQ. ID. No. | Sequence | First Fluorescence luminance | S/N | Second Fluorescence luminance | S/N |
|---|---|---|---|---|---|---|
| PB-3 | 17 | 5' TAAGTAACTATGCACGTCTTGACGGT 3' | 7100 | 98.6 | 7300 | 104.3 |
| PB-4 | 18 | 5' GACCCCTCTAGAGATAGAGTTTTCCC 3' | 4800 | 66.7 | 5200 | 74.3 |
| PB-5 | 19 | 5' AGTAACCATTTGGAGCTAGCCGTC 3' | 9100 | 126.4 | 9300 | 132.9 |
| PB-6 | 20 | 5' GAGCTTGCTCCTCTGACGTTAGC 3' | 5800 | 80.6 | 6300 | 90 |
| PB-7 | 21 | 5' AGCCGGTGGAGTAACCATTTGG 3' | 5400 | 75 | 5500 | 78.6 |

TABLE 24

*Escherichia coli*

| Probe No. | SEQ. ID. No. | Sequence | First Fluorescence luminance | S/N | Second Fluorescence luminance | S/N |
|---|---|---|---|---|---|---|
| PC-1 | 25 | 5' CTCTTGCCATCGGATGTGCCCA 3' | 5600 | 76.7 | 6200 | 83.8 |
| PC-2 | 26 | 5' ATACCTTTGCTCATTGACGTTACCCG 3' | 7600 | 104.1 | 7500 | 101.4 |
| PC-3 | 27 | 5' TTTGCTCATTGACGTTACCCGCAG 3' | 5600 | 76.7 | 5700 | 77 |
| PC-4 | 28 | 5' ACTGGCAAGCTTGAGTCTCGTAGA 3' | 9400 | 128.8 | 9300 | 125.7 |
| PC-5 | 29 | 5' ATACAAAGAGAAGCGACCTCGCG 3' | 7200 | 98.6 | 7200 | 97.3 |
| PC-6 | 30 | 5' CGGACCTCATAAAGTGCGTCGTAGT 3' | 11500 | 157.5 | 11500 | 155.4 |
| PC-7 | 31 | 5' GCGGGGAGGAAGGGAGTAAAGTTAAT 3' | 5600 | 76.7 | 5500 | 74.3 |

TABLE 25

*Klebsiella pneumoniae*

| Probe No. | SEQ. ID. No. | Sequence | First Fluorescence luminance | S/N | Second Fluorescence luminance | S/N |
|---|---|---|---|---|---|---|
| PD-1 | 37 | 5' TAGCACAGAGAGCTTGCTCTCGG 3' | 2000 | 28.6 | 2100 | 30 |
| PD-2 | 38 | 5' TCATGCCATCAGATGTGCCCAGA 3' | 2500 | 35.7 | 2600 | 37.1 |
| PD-3 | 39 | 5' CGGGGAGGAAGGCGATAAGGTTAAT 3' | 2900 | 41.4 | 2900 | 41.4 |
| PD-4 | 40 | 5' TTCGATTGACGTTACCCGCAGAAGA 3' | 4500 | 64.3 | 4700 | 67.1 |
| PD-5 | 41 | 5' GGTCTGTCAAGTCGGATGTGAAATCC 3' | 9900 | 141.4 | 10100 | 144.3 |
| PD-6 | 42 | 5' GCAGGCTAGAGTCTTGTAGAGGGG 3' | 13000 | 185.7 | 13400 | 191.4 |

TABLE 26

Pseudomonas aeruginosa

| Probe No. | SEQ. ID. No. | Sequence | First Fluorescence luminance | S/N | Second Fluorescence luminance | S/N |
|---|---|---|---|---|---|---|
| PE-1 | 48 | 5' TGAGGGAGAAAGTGGGGGATCTTC 3' | 17000 | 239.4 | 17300 | 240.3 |
| PE-2 | 49 | 5' TCAGATGAGCCTAGGTCGGATTAGC 3' | 8300 | 116.9 | 8600 | 119.4 |
| PE-3 | 50 | 5' GAGCTAGAGTACGGTAGAGGGTGG 3' | 17400 | 245.1 | 17000 | 236.1 |
| PE-4 | 51 | 5' GTACGGTAGAGGGTGGTGGAATTTC 3' | 15000 | 211.3 | 16000 | 222.2 |
| PE-5 | 52 | 5' GACCACCTGGACTGATACTGACAC 3' | 8000 | 112.7 | 8300 | 115.3 |
| PE-6 | 53 | 5' TGGCCTTGACATGCTGAGAACTTC 3' | 5400 | 76.1 | 5800 | 80.6 |
| PE-7 | 54 | 5' TTAGTTACCAGCACCTCGGGTGG 3' | 5300 | 74.6 | 5100 | 70.8 |
| PE-8 | 55 | 5' TAGTCTAACCGCAAGGGGACG 3' | 5400 | 76.1 | 5000 | 69.4 |

TABLE 27

Serratia marcescens

| Probe No. | SEQ. ID. No. | Sequence | First Fluorescence luminance | S/N | Second Fluorescence luminance | S/N |
|---|---|---|---|---|---|---|
| PF-1 | 58 | 5' TAGCACAGGGAGCTTGCTCCCT 3' | 3100 | 43.7 | 3300 | 45.2 |
| PF-2 | 59 | 5' AGGTGGTGAGCTTAATACGCTCATC 3' | 3300 | 46.5 | 3200 | 43.8 |
| PF-3 | 60 | 5' TCATCAATTGACGTTACTCGCAGAAG 3' | 10100 | 142.3 | 10000 | 137 |
| PF-4 | 61 | 5' ACTGCATTTGAAACTGGCAAGCTAGA 3' | 12000 | 169 | 11800 | 161.6 |
| PF-5 | 62 | 5' TTATCCTTTGTTGCAGCTTCGGCC 3' | 4100 | 57.7 | 4200 | 57.5 |
| PF-6 | 63 | 5' ACTTTCAGCGAGGAGGAAGGTGG 3' | 14300 | 201.4 | 14300 | 195.9 |

TABLE 28

Streptococcus pneumoniae

| Probe No. | SEQ. ID. No. | Sequence | First Fluorescence luminance | S/N | Second Fluorescence luminance | S/N |
|---|---|---|---|---|---|---|
| PG-1 | 69 | 5' AGTAGAACGCTGAAGGAGGAGCTTG 3' | 4500 | 63.4 | 4300 | 60.6 |
| PG-2 | 70 | 5' CTTGCATCACTACCAGATGGACCTG 3' | 5800 | 81.7 | 5600 | 78.9 |
| PG-3 | 71 | 5' TGAGAGTGGAAAGTTCACACTGTGAC 3' | 5000 | 70.4 | 4900 | 69 |
| PG-4 | 72 | 5' GCTGTGGCTTAACCATAGTAGGCTTT 3' | 8700 | 122.5 | 8800 | 123.9 |
| PG-5 | 73 | 5' AAGCGGCTCTCTGGCTTGTAACT 3' | 7200 | 101.4 | 7300 | 102.8 |
| PG-6 | 74 | 5' TAGACCCTTTCCGGGGTTTAGTGC 3' | 6700 | 94.4 | 7000 | 98.6 |
| PG-7 | 75 | 5' GACGGCAAGCTAATCTCTTAAAGCCA 3' | 10200 | 143.7 | 9900 | 139.4 |

TABLE 29

Haemophilus influenzae

| Probe No. | SEQ. ID. No. | Sequence | First Fluorescence luminance | S/N | Second Fluorescence luminance | S/N |
|---|---|---|---|---|---|---|
| PH-1 | 78 | 5'GCTTGGGAATCTGGCTTATGGAGG 3' | 3100 | 44.3 | 3200 | 45.1 |
| PH-2 | 79 | 5'TGCCATAGGATGAGCCCAAGTGG 3' | 3200 | 45.7 | 3200 | 45.1 |
| PH-3 | 80 | 5'CTTGGGAATGTACTGACGCTCATGTG 3' | 4900 | 70 | 3600 | 78.9 |
| PH-4 | 81 | 5'GGATTGGGCTTAGAGCTTGGTGC 3' | 3900 | 55.7 | 3800 | 53.5 |
| PH-5 | 82 | 5'TACAGAGGGAAGCGAAGCTGCG 3' | 6700 | 95.7 | 6500 | 91.5 |
| PH-6 | 83 | 5'GGCGTTTACCACGGTATGATTCATGA 3' | 10200 | 145.7 | 11000 | 154.9 |
| PH-7 | 84 | 5'AATGCCTACCAAGCCTGCGATCT 3' | 4200 | 60 | 4100 | 57.7 |
| PH-8 | 85 | 5'TATCGGAAGATGAAAGTGCGGGACT 3' | 3200 | 45.7 | 3500 | 49.3 |

TABLE 30

Enterobacter cloacae

| Probe No. | SEQ. ID. No. | Sequence | First Fluorescence luminance | S/N | Second Fluorescence luminance | S/N |
|---|---|---|---|---|---|---|
| PI-1 | 86 | 5' CAGAGAGCTTGCTCTCGGGTGA 3' | 10000 | 133.3 | 9900 | 133.8 |
| PI-2 | 87 | 5'GGGAGGAAGGTGTTGTGGTTAATAAC 3' | 38000 | 506.7 | 38000 | 513.5 |
| PI-3 | 88 | 5'GGTGTTGTGGTTAATAACCACAGCAA 3' | 4700 | 62.7 | 4700 | 63.5 |
| PI-4 | 89 | 5'GCGGTCTGTCAAGTCGGATGTG 3' | 31000 | 413.3 | 32000 | 432.4 |
| PI-5 | 90 | 5'ATTCGAAACTGGCAGGCTAGAGTCT 3' | 47500 | 633.3 | 45000 | 608.1 |
| PI-6 | 91 | 5'TAACCACAGCAATTGACGTTACCCG 3' | 23600 | 314.7 | 24000 | 324.3 |
| PI-7 | 92 | 5'GCAATTGACGTTACCCGCAGAAGA 3' | 21500 | 286.7 | 22700 | 306.8 |

TABLE 31

Enterococcus faecalis

| Probe No. | SEQ. ID. No. | Sequence | First Fluorescence luminance | S/N | Second Fluorescence luminance | S/N |
|---|---|---|---|---|---|---|
| PJ-1 | 98 | 5'TTCTTTCCTCCCGAGTGCTTGCA 3' | 7000 | 98.6 | 7300 | 101.4 |
| PJ-2 | 99 | 5'AACACGTGGGTAACCTACCCATCAG 3' | 12300 | 173.2 | 12000 | 166.7 |
| PJ-3 | 100 | 5'ATGGCATAAGAGTGAAAGGCGGCTT 3' | 25000 | 352.1 | 27400 | 380.6 |
| PJ-4 | 101 | 5'GACCCGCGGTGCATTAGCTAGT 3' | 10000 | 140.8 | 11000 | 152.8 |
| PJ-5 | 102 | 5'GGACGTTAGTAACTGAACGTCCCCT 3' | 5600 | 78.9 | 5200 | 72.2 |
| PJ-6 | 103 | 5'CTCAACCGGGGAGGGTCATTGG 3' | 22100 | 311.3 | 22200 | 308.3 |
| PJ-7 | 104 | 5'TTGGAGGGTTTCCGCCCTTCAG 3' | 8800 | 123.9 | 9000 | 125 |

The numerical values of florescent luminances (photomultiplier voltage: 400 V) in Tables 22 to 31 indicate average pixel luminances (resolution: 5 μm). The S/N ratios indicate values obtained by dividing the fluorescent luminances by background average values measured by analysis software (GenePix Pro Ver.3.0 available from Axon) attached to the measuring device.

As is apparent from Tables 22 to 31, the respective etiologic agents can be detected with sufficient signals at a high reproducibility.

Example 3

Microorganism Detection Using 2-Step PCR

As in Examples 1 and 2, probe DNAs, specimen amplification PCR primers, the genome DNAs of etiologic agents, and DNA microarrays were prepared, and the following experiments were conducted.

1. Amplification and Labeling of Specimens (Utilization of PCR Amplification with Fluorescent Labeling)

Amplification of microbial genes as specimens (1st PCR) and labeling (2nd PCR) reaction will be described below.

2. Amplification Reaction Solution Composition: 1st PCR

| | | |
|---|---|---|
| AmpliTaq Gold LD(5U/μL) | 0.5 μL | |
| Template DNA | variable | |
| dNTP mis(2.5 mM/each) | 4.0 μL | |
| ×10 PCR buffer | 5.0 μL | |
| 25 mM MgCl$_2$ | 7.0 μL | |
| Forward Primer Mix(10 μM/each) | 0.25 μL | |
| Reverse Primer Mix(10 μM/each) | 0.25 μL | |
| H$_2$O | variable | |
| Total | 50 μL | |

Amplification reaction of the reaction solution having the above composition was caused by using a commercially available thermal cycler in accordance with the following protocol.

| | |
|---|---|
| 95° C. | 10 min. |

39 Cycles

| | |
|---|---|
| 72° C. | 45 sec. |
| 72° C. | 10 min. |

After the end of reaction, purification was performed by using a purification column (QIAquick PCR Purification Kit available from QIAGEN). Then, determination of the amplified products was executed.

3. Labeling Reaction Composition: 2nd PCR

| | | |
|---|---|---|
| Premix PCR reagent(TAKARA ExTaq) | 25 μl | |
| Template DNA (1st PCR Product) | Variable | (30 ng/tube) |
| Cy3 Labeled Reverse primer Mix | 5 μl | |
| H$_2$0 | Variable | |
| Total | 50 μl | |

Amplification reaction of the reaction solution having the above composition was caused by using a commercially available thermal cycler in accordance with the following protocol.

| | |
|---|---|
| 95° C. | 10 min. |

| | |
|---|---|
| 72° C. | 45 sec. |
| 72° C. | 10 min. |

After the end of reaction, purification was performed by using a purification column (QIAquick PCR Purification Kit available from QIAGEN) to obtain labeled specimens.

4. Hybridization

Hybridization was done in accordance with the same procedures as in Example 1.

5. Microorganism Detection (Fluorometry)

Fluorometry was executed for the DNA microarrays after the end of hybridization reaction by using a DNA microarray fluorescent detector (GenePix 4000B available from Axon). Tables 32 to 41 show the measurement results.

Note that, in this example, fluorometry was executed once twice for each DNA microarray. The results are shown in Tables 32 to 41.

TABLE 32

Staphylococcus aureus

| Probe No. | SEQ. ID. No. | Sequence | First Fluorescence luminance | S/N | Second Fluorescence luminance | S/N |
|---|---|---|---|---|---|---|
| PA-10 | 10 | 5' ACGGACGAGAAGCTTGCTTCTCT 3' | 247 | 3.4 | 146 | 2.1 |
| PA-11 | 11 | 5' TGTCACTTATAGATGGATCCGCGCT 3' | 4177 | 57.9 | 3083 | 43.4 |
| PA-12 | 12 | 5' TGTAAGTAACTGTGCACATCTTGACG 3' | 4686 | 64.9 | 3768 | 53.1 |
| PA-13 | 13 | 5' ACAACTCTAGAGATAGAGCCTTCCCC 3' | 2612 | 36.2 | 2709 | 38.2 |
| PA-14 | 14 | 5' GTGGAGTAACCTTTTAGGAGCTAGCC 3' | 26505 | 367.2 | 17560 | 247.3 |

TABLE 33

Staphylococcus epidermidis

| Probe No. | SEQ. ID. No. | Sequence | First Fluorescence luminance | S/N | Second Fluorescence luminance | S/N |
|---|---|---|---|---|---|---|
| PB-2 | 16 | 5' TAGTGAAAGACGGTTTTGCTGTCACT 3' | 7000 | 94.1 | 1800 | 25.7 |
| PB-4 | 18 | 5' GACCCCTCTAGAGATAGAGTTTTCCC 3' | 3274 | 44.0 | 1100 | 15.7 |
| PB-8 | 22 | 5' AGACGAGGAGCTTGCTCCTCTG 3' | 111 | 1.5 | 59 | 0.8 |
| PB-9 | 23 | 5' AGAACAAATGTGTAAGTAACTATGCACGT 3' | 6920 | 93.0 | 4910 | 70.1 |
| Pb-10 | 24 | 5' ACCATTTGGAGCTAGCCGTCGA 3' | 15244 | 205.0 | 18136 | 259.1 |

TABLE 34

Escherichia coli

| Probe No. | SEQ. ID. No. | Sequence | First Fluorescence luminance | S/N | Second Fluorescence luminance | S/N |
|---|---|---|---|---|---|---|
| PC-4 | 28 | 5' ACTGGCAAGCTTGAGTCTCGTAGA 3' | 5416 | 74.7 | 2100 | 31.3 |
| PC-8 | 32 | 5' TAACAGGAAGAAGCTTGCTTCTTTGCTG 3' | 160 | 2.2 | 112 | 1.7 |
| PC-9 | 33 | 5' TTGCCATCGGATGTGCCCAGAT 3' | 4133 | 57.0 | 4581 | 68.4 |
| PC-10 | 34 | 5' GGAAGGGAGTAAAGTTAATACCTTTGCTC 3' | 4194 | 57.8 | 5349 | 79.8 |
| PC-11 | 35 | 5' ATCTTTTGTTGCCAGCGGTCCG 3' | 6719 | 92.7 | 2594 | 38.7 |
| PC-12 | 36 | 5' AAGGGAGTAAAGTTAATACCTTTGCTCATTG 3' | 3984 | 58.6 | 4021 | 60.0 |

TABLE 35

Klebsiella pneumoniae

| Probe No. | SEQ. ID. No. | Sequence | First Fluorescence luminance | S/N | Second Fluorescence luminance | S/N |
|---|---|---|---|---|---|---|
| PD-7 | 43 | 5' TCATGCCATCAGATGTGCCCAGAT 3' | 5414 | 40.0 | 4171 | 62.3 |
| PD-8 | 44 | 5' CGGGGAGGAAGGCGATAAGGTTAA 3' | 4096 | 30.2 | 6227 | 93.0 |

TABLE 35-continued

| | | Klebsiella pneumoniae | | | | |
|---|---|---|---|---|---|---|
| | | | First | | Second | |
| Probe No. | SEQ. ID. No. | Sequence | Fluo-rescence luminance | S/N | Fluo-rescence luminance | S/N |
| PD-9 | 45 | 5' TTATCGATTGACGTTACCCGCAGAAGA 3' | 4122 | 30.4 | 3269 | 48.8 |
| PD-10 | 46 | 5' CATTCGAAACTGGCAGGCTAGAGTC 3' | 9474 | 70.0 | 6486 | 96.9 |
| PD-11 | 47 | 5' CCTTTGTTGCCAGCGGTTAGGC 3' | 10648 | 78.6 | 2754 | 41.1 |

TABLE 36

| | | Pseudomonas aeruginosa | | | | |
|---|---|---|---|---|---|---|
| | | | First | | Second | |
| Probe No. | SEQ. ID. No. | Sequence | Fluo-rescence luminance | S/N | Fluo-rescence luminance | S/N |
| PE-1 | 48 | 5' TGAGGGAGAAAGTGGGGGATCTTC 3' | 6175 | 82.2 | 3600 | 50.0 |
| PE-6 | 53 | 5' TGGCCTTGACATGCTGAGAACTTTC 3' | 8159 | 108.6 | 1200 | 16.7 |
| PE-7 | 54 | 5' TTAGTTACCAGCACCTCGGGTGG 3' | 3277 | 43.6 | 1200 | 16.7 |
| PE-8 | 55 | 5' TGCATCCAAAACTACTGAGCTAGAGTAC 3' | 6626 | 88.2 | 7432 | 103.4 |
| PE-9 | 56 | 5' GTCGACTAGCCGTTGGGATCCT 3' | 5734 | 76.3 | 3365 | 46.8 |

TABLE 37

| | | Serratia marcescens | | | | |
|---|---|---|---|---|---|---|
| | | | First | | Second | |
| Probe No. | SEQ. ID. No. | Sequence | Fluo-rescence luminance | S/N | Fluo-rescence luminance | S/N |
| PF-7 | 64 | 5' GGTAGCACAGGGGAGCTTGCTC 3' | 4482 | 66.4 | 1040 | 15.1 |
| PF-8 | 65 | 5' CGAGGAGGAAGGTGGTGAGCTTAATA 3' | 6362 | 94.2 | 3199 | 46.3 |
| PF-9 | 66 | 5' TACGCTCATCAATTGACGTTACTCGC 3' | 4569 | 67.7 | 2884 | 41.8 |
| PF-10 | 67 | 5' GAAACTGGCAAGCTAGAGTCTCGTAGA 3' | 7905 | 117.1 | 6786 | 98.3 |
| PF-11 | 68 | 5' TTATCCTTTGTTGCCAGCGGTTCG 3' | 12787 | 189.4 | 4849 | 55.7 |

TABLE 38

| | | Streptococcus pneumoniae | | | | |
|---|---|---|---|---|---|---|
| | | | First | | Second | |
| Probe No. | SEQ. ID. No. | Sequence | Fluo-rescence luminance | S/N | Fluo-rescence luminance | S/N |
| PG-1 | 69 | 5' AGTAGAACGCTGAAGGAGGAGCTTG 3' | 10078 | 70.3 | 1100 | 16.2 |
| PG-5 | 73 | 5' AAGCGGCTCTCTGGCTTGTAACT 3' | 4331 | 30.2 | 1500 | 22.1 |
| PG-6 | 74 | 5' TAGACCCTTTCCGGGGTTTAGTGC 3' | 4730 | 33.0 | 1300 | 19.1 |

TABLE 38-continued

| | | Streptococcus pneumoniae | | | | |
|---|---|---|---|---|---|---|
| | | | First | | Second | |
| Probe No. | SEQ. ID. No. | Sequence | Fluorescence luminance | S/N | Fluorescence luminance | S/N |
| PG-8 | 76 | 5' GACATTTGCTTAAAAGGTGCACTTGCA 3' | 7128 | 49.7 | 7720 | 113.6 |
| PG-9 | 77 | 5' GTTGTAAGAGAAGAACGAGTGTGAGAGTG 3' | 6665 | 46.5 | 3297 | 48.5 |

TABLE 39

| | | Haemophilus influenzae | | | | |
|---|---|---|---|---|---|---|
| | | | First | | Second | |
| Probe No. | SEQ. ID. No. | Sequence | Fluorescence luminance | S/N | Fluorescence luminance | S/N |
| PH-1 | 78 | 5' GCTTGGGAATCTGGCTTATGGAGG 3' | 11106 | 150.3 | 3600 | 50.0 |
| PH-2 | 79 | 5' TGCCATAGGATGAGCCCAAGTGG 3' | 7056 | 95.5 | 700 | 10.1 |
| PH-4 | 81 | 5' GGATTGGGCTTAGAGCTTGGTGC 3' | 100 | 1.4 | 1200 | 17.4 |
| PH-5 | 82 | 5' TACAGAGGGAAGCGAAGCTGCG 3' | 11237 | 152.1 | 600 | 8.7 |
| PH-7 | 84 | 5' AATGCCTACCAAGCCTGCGATCT 3' | 5054 | 68.4 | 2200 | 31.9 |

TABLE 40

| | | Enterobacter cloacae | | | | |
|---|---|---|---|---|---|---|
| | | | First | | Second | |
| Probe No. | SEQ. ID. No. | Sequence | Fluorescence luminance | S/N | Fluorescence luminance | S/N |
| PI-8 | 93 | 5' GTAGCACAGAGAGCTTGCTCTCG 3' | 2221 | 30.1 | 582 | 8.2 |
| PI-9 | 94 | 5' CGGGGAGGAAGGTGTTGTGGTTA 3' | 5484 | 74.2 | 2193 | 30.9 |
| PI-10 | 95 | 5' ACCACAGCAATTGACGTTACCCG 3' | 3325 | 45.0 | 646 | 9.1 |
| PI-11 | 96 | 5' GAAACTGGCAGGCTAGAGTCTTGTAG 3' | 7574 | 102.5 | 3039 | 42.8 |
| PI-12 | 97 | 5' AGGCGGTCTGTCAAGTCGGATG 3' | 5768 | 78.0 | 5701 | 80.3 |

TABLE 41

| | | Enterococcus faecalis | | | | |
|---|---|---|---|---|---|---|
| | | | First | | Second | |
| Probe No. | SEQ. ID. No. | Fluorescence | Fluorescence luminance | S/N | Fluorescence luminance | S/N |
| PJ-1 | 98 | 5' TTCTTTCCTCCCGAGTGCTTGCA 3' | 1012 | 14.9 | 1500 | 20.8 |
| PJ-3 | 100 | 5' ATGGCATAAGAGTGAAAGGCGCTT 3' | 4266 | 62.6 | 5600 | 77.8 |
| PJ-5 | 102 | 5' GGACGTTAGTAACTGAACGTCCCCT 3' | 652 | 9.6 | 1400 | 19.4 |
| PJ-8 | 105 | 5' ATAGAGCTTTCCCTTCGGGGACAAA 3' | 3232 | 47.5 | 810 | 11.2 |
| PJ-9 | 106 | 5' CGAGGTCATGCAAATCTCTTAAAGCTTCT 3' | 11411 | 167.6 | 18776 | 260.7 |

As is apparent from Tables 32 to 41, the respective etiologic agents can be detected with sufficient signals at a high reproducibility.

As described above, according to the examples, an infectious etiologic agent can be identified by using microarrays on which probe sets capable of detecting the 10 bacteria, i.e., *Staphylococcus aureus, Staphylococcus epidermidis, Escherichia coli, Klebsiella pneumoniae, Pseudomonas aeruginosa, Serratia marcescens, Streptococcus pneumoniae, Haemophilus influenzae, Enterobacter cloacae,* and *Enterococcus faecalis* are separately immobilized or combined. Hence, the problems of the DNA probe of microbial origin are solved. More specifically, because of the small number of bases, oligonucleotide probes can chemically be mass-produced, and purification and concentration control are possible. In addition, a probe set can be provided, which allows to detect bacteria in the same species all together and discriminatingly detect bacteria in other species for the purpose of classifying the bacteria depending on the species.

Furthermore, a probe set can be provided, which also considers the stability of a hybrid body between a probe and a specimen so that the difference between the species can accurately be evaluated on a DNA microarray. A carrier on which the probe DNAs are immobilized to make the probe DNAs react with specimens can also be provided. Also, a carrier can be provided, on which the probe DNAs are chemically immobilized so that the probe DNAs are stably immobilized on the carrier, and a detection result with high reproducibility can be obtained in the process of reaction between a specimen solution and the probes and probe sets.

According to the above examples, 16s rRNA gene arrangements in the genes of infectious etiologic agents can be detected in proper quantities. Hence, the presence of an infectious etiologic agent can efficiently and accurately be determined.

Example 4

Primer Set

The primer sets (Table 11) used in the above examples to amplify the 16s rRNA gene arrangements of one or some of *Staphylococcus aureus, Staphylococcus epidermidis, Escherichia coli, Klebsiella pneumoniae, Pseudomonas aeruginosa, Serratia marcescens, Streptococcus pneumoniae, Haemophilus influenzae, Enterobacter cloacae,* and *Enterococcus faecalis* will be described.

The primer sets of this example are designed to give a satisfactory amplification result in PCR reaction executed to identify an infectious etiologic agent. "Satisfactory" means not only that the target 16s rRNAs are sufficiently amplified but also that no products other than the 16s rRNAs are generated.

"Satisfactory" also means that only the 16s rRNAs of an infectious etiologic agent are amplified without amplifying human genome genes originated in a specimen, which are contained in the specimen.

Any specimen in which bacteria may be present, and for example, body fluids originated in animals such as human and livestock, including blood, spinal fluid, phlegm, stomach fluid, vaginal discharge, and intraoral mucus, and excretion such as urine and feces are used in this example. All media which can be contaminated by bacteria can also be used in this example, including food, drink water and hot spring water in the natulal environment, which may cause food poisoning by contamination, filters from air and water cleaners, and so forth. Animals and plants which should be quarantined in import/export are also used as specimens.

The PCR reaction used in this example includes PCR reaction which uses an extracted nucleic acid itself as a template, asymmetrical PCR reaction which uses primers on one side of SEQ ID Nos. 107 to 109 (F1 to F3 in Table 11) or SEQ ID Nos. 110 to 112 (R1 to R3 in Table 11), and PCR which executes labeling for visualization.

1. Preparation of Specimen Amplification PCR Primers

As 16s rRNA gene (target gene) amplification PCR primers for etiologic agent detection, nucleic acid sequences shown in Table 11 were designed.

More specifically, probe sets which specifically amplify the genome parts coding the 16s rRNAs, i.e., primers for which the specific melting points were made uniform as much as possible at the two end portions of the 16s rRNA coding region of a base length of 1,500 were designed. In order to simultaneously amplify variants or a plurality of 16s rRNA coding regions on genomes, a plurality of kinds of primers were designed.

The primers shown in Table 11 were purified by HPLC (High Performance Liquid Chromatography) after synthesis. All of three forward primers and three reverse primers were mixed and dissolved in a TE buffer solution such that each primer concentration had an ultimate concentration of 10 pmol/µl. In this example, all the forward primers and reverse primers were used. Alternatively, one to three forward primers and one to three reverse primers may be used.

By using a thus prepared solution of forward primers and reverse primers (forward primer mix and reverse primer mix), genome DNAs extracted by the method described in [3. Extraction of Genome DNAs (Model Specimens) of Etiologic Agents] were amplified by the method described in [5. Amplification and Labeling of Specimens (PCR Amplification & Fluorescent Labeling)].

After the end of reaction, the primers were removed by using a purification column (QIAquick PCR Purification Kit available from QIAGEN). Then, the amplified products were examined by gel electrophoresis. One band was detected in 1,500 base pair regions, and it was confirmed that satisfactory PCR reaction was executed. No byproducts were generated.

When the primers shown in Table 11 were used, satisfactory PCR amplification results were obtained in, e.g., all of the above-described 10 infectious etiologic agents (*Staphylococcus aureus, Staphylococcus epidermidis, Escherichia Coli, Klebsiella pneumoniae, Pseudomonas aeruginosa, Serratia marcescens, Streptococcus pneumoniae, Haemophilus influenzae, Enterobacter cloacae,* and *Enterococcus faecalis*).

Example 5

Amplification of 16s rRNA Genes from Mixture of Blood and Broth

Bacteremia model systems were prepared by adding $10^3$, $10^4$, and $10^5$ *Enterobacter cloacae*, which was cultured in accordance with the procedures described in Example 1, to 200-µl human blood (collected EDTA blood). An N-acetyl muramidase solution (0.2 mg/ml in Enzyme Buffer) was added to each solution. The solutions were heated to 37° C. for 30 min. After that, DNAs were extracted by using Qiamp Blood mini Kit (available from QIAGEN) to prepare templates for PCR reaction.

PCR reaction was caused for these DNAs by using the primers shown in Table 11, as in Example 4.

As a result, as in Example 4, one band was detected in 1,500 base pair regions, and it was confirmed that satisfactory PCR reaction was executed. No byproducts were generated. The amount of PCR amplified products obtained from the band was proportional to the added cell amount. This indicates that when the primer sets were used, only the 16s rRNAs of *Enterobacter cloacae* were amplified without generating any PCR byproduct of human genome.

As described above, according to this example, the 16s rRNA parts in the genes of a plurality of kinds of infectious etiologic agents can efficiently be amplified at a high purity. In addition, even when human genome DNAs are present, only the 16s rRNAs of an infectious etiologic agent can efficiently be amplified.

As has been described above, according to the present invention, an infection detection probe which allows mass preparation at a time and identification of a species in similar species can be provided. More specifically, an infection detection probe which can suitably be used to classify a plurality of kinds of etiologic agents of an infection on the basis of the species can be provided.

Alternatively, an infection detection probe suitable for detection of, e.g., the above-described 10 bacteria as the etiologic agents of infections can be provided.

A probe set can also be provided, which also considers the stability of a hybrid body between an infection detection probe and a specimen so that the difference between similar species can accurately be evaluated on a DNA chip.

In addition, a carrier on which the infection detection probe is immobilized to make the infection detection probe react with the specimen can be provided.

Furthermore, a carrier can be provided, on which the infection detection probes are chemically immobilized so that the infection detection probes are stably immobilized on the carrier, and a detection result with high reproducibility can be obtained in the process of reaction with a specimen solution.

According to the present invention, there is also provided a PCR reaction primer which amplifies the 16s rRNAs of an etiologic agent in a specimen in order to detect and/or identify an infectious etiologic agent.

According to the present invention, there is also provided a primer set which can commonly be used for a plurality of species and effectively amplify the 16s rRNAs of an etiologic agent even when the species is unknown.

According to the present invention, there is also provided a primer set which can amplify the 16s rRNAs of a plurality of kinds of etiologic agents under the same PCR conditions.

As many apparently widely different embodiments of the present invention can be made without departing from the spirit and scope thereof, it is to be understood that the invention is not limited to the specific embodiments thereof except as defined in the appended claims.

What is claimed is:

1. A probe set of infection detection probes each of which can detect an existence of a 16s rRNA gene originating in *Staphylococcus aureus* in a sample in which one or more of *Staphylococcus aureus, Staphylococcus epidermidis, Escherichia coli, Klebsiella pneumoniae, Pseudomonas aeruginosa, Serratia marcescens, Streptococcus pneumoniae, Haemophilus influenzae, Enterobacter cloacae* and *Enterococcus faecalis* possibly exists, wherein the probe set comprises nine oligonucleotides, each consisting of a different one of the following base sequences (A) to (I):
(A) SEQ ID No. 1 or the complementary sequence thereof;
(B) SEQ ID No. 2 or the complementary sequence thereof;
(C) SEQ ID No. 3 or the complementary sequence thereof;
(D) SEQ ID No. 4 or the complementary sequence thereof;
(E) SEQ ID No. 5 or the complementary sequence thereof;
(F) SEQ ID No. 6 or the complementary sequence thereof;
(G) SEQ ID No. 7 or the complementary sequence thereof;
(H) SEQ ID No. 8 or the complementary sequence thereof; and
(I) SEQ ID No. 9 or the complementary sequence thereof.

2. A probe set which can detect an existence of a 16s rRNA gene originating in *Staphylococcus aureus*, the probe set consisting of different types of oligonucleotides, wherein the different types of oligonucleotides consist of nine oligonucleotides, each consisting of a different one of the following base sequences (A) to (I):
(A) SEQ ID No. 1 or the complementary sequence thereof;
(B) SEQ ID No. 2 or the complementary sequence thereof;
(C) SEQ ID No. 3 or the complementary sequence thereof;
(D) SEQ ID No. 4 or the complementary sequence thereof;
(E) SEQ ID No. 5 or the complementary sequence thereof;
(F) SEQ ID No. 6 or the complementary sequence thereof;
(G) SEQ ID No. 7 or the complementary sequence thereof;
(H) SEQ ID No. 8 or the complementary sequence thereof; and
(I) SEQ ID No. 9 or the complementary sequence thereof.

3. A carrier on which the probe set according to claim 1 or 2 is chemically immobilized.

4. A method of detecting a gene originating in *Staphylococcus aureus* in a specimen in which bacteria may be present comprising reacting the carrier of claim 3 with the specimen and detecting the gene originating in *Staphylococcus aureus* based on hybridization of the probe set on the carrier with the specimen.

5. The probe set according to claim 1, wherein the probe set comprises fourteen oligonucleotides, each consisting of a different one of the following base sequences (A) to (N):
(A) SEQ ID No. 1 or the complementary sequence thereof;
(B) SEQ ID No. 2 or the complementary sequence thereof;
(C) SEQ ID No. 3 or the complementary sequence thereof;
(D) SEQ ID No. 4 or the complementary sequence thereof;
(E) SEQ ID No. 5 or the complementary sequence thereof;
(F) SEQ ID No. 6 or the complementary sequence thereof;
(G) SEQ ID No. 7 or the complementary sequence thereof;
(H) SEQ ID No. 8 or the complementary sequence thereof;
(I) SEQ ID No. 9 or the complementary sequence thereof
(J) SEQ ID No. 10 or the complementary sequence thereof;
(K) SEQ ID No. 11 or the complementary sequence thereof;

(L) SEQ ID No. 12 or the complementary sequence thereof;
(M) SEQ ID No. 13 or the complementary sequence thereof; and
(N) SEQ ID No. 14 or the complementary sequence thereof.

6. An array on which the probe set according to claim 1 is immobilized, wherein the probe set includes the only probes on the array for detecting *Staphylococcus aureus*.

* * * * *

SEQUENCE LISTING

```
<160> NUMBER OF SEQ ID NOS: 218

<210> SEQ ID NO 1
<211> LENGTH: 26
<212> TYPE: DNA
<213> ORGANISM: Artificial
<220> FEATURE:
<223> OTHER INFORMATION: Synthesized DNA probe named PA-1

<400> SEQUENCE: 1
gaaccgcatg gttcaaaagt gaaaga                                        26

<210> SEQ ID NO 2
<211> LENGTH: 24
<212> TYPE: DNA
<213> ORGANISM: Artificial
<220> FEATURE:
<223> OTHER INFORMATION: Synthesized DNA probe named PA-2

<400> SEQUENCE: 2
cacttataga tggatccgcg ctgc                                          24

<210> SEQ ID NO 3
<211> LENGTH: 26
<212> TYPE: DNA
<213> ORGANISM: Artificial
<220> FEATURE:
<223> OTHER INFORMATION: Synthesized DNA probe named PA-3

<400> SEQUENCE: 3
tgcacatctt gacggtacct aatcag                                        26

<210> SEQ ID NO 4
<211> LENGTH: 22
<212> TYPE: DNA
<213> ORGANISM: Artificial
```

```
<220> FEATURE:
<223> OTHER INFORMATION: Synthesized DNA probe named PA-4

<400> SEQUENCE: 4
ccccttagtg ctgcagctaa cg                                              22

<210> SEQ ID NO 5
<211> LENGTH: 23
<212> TYPE: DNA
<213> ORGANISM: Artificial
<220> FEATURE:
<223> OTHER INFORMATION: Synthesized DNA probe named PA-5

<400> SEQUENCE: 5
aatacaaagg gcagcgaaac cgc                                             23

<210> SEQ ID NO 6
<211> LENGTH: 25
<212> TYPE: DNA
<213> ORGANISM: Artificial
<220> FEATURE:
<223> OTHER INFORMATION: Synthesized DNA probe named PA-6

<400> SEQUENCE: 6
ccggtggagt aaccttttag gagct                                           25

<210> SEQ ID NO 7
<211> LENGTH: 25
<212> TYPE: DNA
<213> ORGANISM: Artificial
<220> FEATURE:
<223> OTHER INFORMATION: Synthesized DNA probe named PA-7

<400> SEQUENCE: 7 taaccttttta ggagctagcc gtcga                                          25

<210> SEQ ID NO 8
<211> LENGTH: 23
<212> TYPE: DNA
<213> ORGANISM: Artificial
<220> FEATURE:
<223> OTHER INFORMATION: Synthesized DNA probe named PA-8

<400> SEQUENCE: 8
tttaggagct agccgtcgaa ggt                                             23

<210> SEQ ID NO 9
<211> LENGTH: 23
<212> TYPE: DNA
<213> ORGANISM: Artificial
<220> FEATURE:
<223> OTHER INFORMATION: Synthesized DNA probe named PA-9

<400> SEQUENCE: 9
tagccgtcga aggtgggaca aat                                             23

<210> SEQ ID NO 10
<211> LENGTH: 23
<212> TYPE: DNA
<213> ORGANISM: Artificial
<220> FEATURE:
<223> OTHER INFORMATION: Synthesized DNA probe named PA-10

<400> SEQUENCE: 10
acggacgaga agcttgcttc tct                                             23
```

```
<210> SEQ ID NO 11
<211> LENGTH: 25
<212> TYPE: DNA
<213> ORGANISM: Artificial
<220> FEATURE:
<223> OTHER INFORMATION: Synthesized DNA probe named PA-11

<400> SEQUENCE: 11
tgtcacttat agatggatcc gcgct                                         25

<210> SEQ ID NO 12
<211> LENGTH: 26
<212> TYPE: DNA
<213> ORGANISM: Artificial
<220> FEATURE:
<223> OTHER INFORMATION: Synthesized DNA probe named PA-12

<400> SEQUENCE: 12
tgtaagtaac tgtgcacatc ttgacg                                        26

<210> SEQ ID NO 13
<211> LENGTH: 26
<212> TYPE: DNA
<213> ORGANISM: Artificial
<220> FEATURE:
<223> OTHER INFORMATION: Synthesized DNA probe named PA-13

<400> SEQUENCE: 13
acaactctag agatagagcc ttcccc                                        26

<210> SEQ ID NO 14
<211> LENGTH: 26
<212> TYPE: DNA
<213> ORGANISM: Artificial
<220> FEATURE:
<223> OTHER INFORMATION: Synthesized DNA probe named PA-14

<400> SEQUENCE: 14
gtggagtaac cttttaggag ctagcc                                        26

<210> SEQ ID NO 15
<211> LENGTH: 22
<212> TYPE: DNA
<213> ORGANISM: Artificial
<220> FEATURE:
<223> OTHER INFORMATION: Synthesized DNA probe named PB-1

<400> SEQUENCE: 15
gaacagacga ggagcttgct cc                                            22

<210> SEQ ID NO 16
<211> LENGTH: 26
<212> TYPE: DNA
<213> ORGANISM: Artificial
<220> FEATURE:
<223> OTHER INFORMATION: Synthesized DNA probe named PB-2

<400> SEQUENCE: 16
tagtgaaaga cggttttgct gtcact                                        26

<210> SEQ ID NO 17
<211> LENGTH: 26
<212> TYPE: DNA
<213> ORGANISM: Artificial
<220> FEATURE:
<223> OTHER INFORMATION: Synthesized DNA probe named PB-3

<400> SEQUENCE: 17
```

```
taagtaacta tgcacgtctt gacggt                                          26

<210> SEQ ID NO 18
<211> LENGTH: 26
<212> TYPE: DNA
<213> ORGANISM: Artificial
<220> FEATURE:
<223> OTHER INFORMATION: Synthesized DNA probe named PB-4

<400> SEQUENCE: 18
gacccctcta gagatagagt tttccc                                          26

<210> SEQ ID NO 19
<211> LENGTH: 24
<212> TYPE: DNA
<213> ORGANISM: Artificial
<220> FEATURE:
<223> OTHER INFORMATION: Synthesized DNA probe named PB-5

<400> SEQUENCE: 19
agtaaccatt tggagctagc cgtc                                            24

<210> SEQ ID NO 20
<211> LENGTH: 23
<212> TYPE: DNA
<213> ORGANISM: Artificial
<220> FEATURE:
<223> OTHER INFORMATION: Synthesized DNA probe named PB-6

<400> SEQUENCE: 20
gagcttgctc ctctgacgtt agc                                             23

<210> SEQ ID NO 21
<211> LENGTH: 22
<212> TYPE: DNA
<213> ORGANISM: Artificial
<220> FEATURE:
<223> OTHER INFORMATION: Synthesized DNA probe named PB-7

<400> SEQUENCE: 21
agccggtgga gtaaccattt gg                                              22

<210> SEQ ID NO 22
<211> LENGTH: 22
<212> TYPE: DNA
<213> ORGANISM: Artificial
<220> FEATURE:
<223> OTHER INFORMATION: Synthesized DNA probe named PB-8

<400> SEQUENCE: 22
agacgaggag cttgctcctc tg                                              22

<210> SEQ ID NO 23
<211> LENGTH: 29
<212> TYPE: DNA
<213> ORGANISM: Artificial
<220> FEATURE:
<223> OTHER INFORMATION: Synthesized DNA probe named PB-9

<400> SEQUENCE: 23
agaacaaatg tgtaagtaac tatgcacgt                                       29

<210> SEQ ID NO 24
<211> LENGTH: 22
<212> TYPE: DNA
<213> ORGANISM: Artificial
```

```
<220> FEATURE:
<223> OTHER INFORMATION: Synthesized DNA probe named PB-10

<400> SEQUENCE: 24
accatttgga gctagccgtc ga                                              22

<210> SEQ ID NO 25
<211> LENGTH: 22
<212> TYPE: DNA
<213> ORGANISM: Artificial
<220> FEATURE:
<223> OTHER INFORMATION: Synthesized DNA probe named PC-1

<400> SEQUENCE: 25
ctcttgccat cggatgtgcc ca                                              22

<210> SEQ ID NO 26
<211> LENGTH: 26
<212> TYPE: DNA
<213> ORGANISM: Artificial
<220> FEATURE:
<223> OTHER INFORMATION: Synthesized DNA probe named PC-2

<400> SEQUENCE: 26
atacctttgc tcattgacgt tacccg                                          26

<210> SEQ ID NO 27
<211> LENGTH: 24
<212> TYPE: DNA
<213> ORGANISM: Artificial
<220> FEATURE:
<223> OTHER INFORMATION: Synthesized DNA probe named PC-3

<400> SEQUENCE: 27
tttgctcatt gacgttaccc gcag                                            24

<210> SEQ ID NO 28
<211> LENGTH: 24
<212> TYPE: DNA
<213> ORGANISM: Artificial
<220> FEATURE:
<223> OTHER INFORMATION: Synthesized DNA probe named PC-4

<400> SEQUENCE: 28
actggcaagc ttgagtctcg taga                                            24

<210> SEQ ID NO 29
<211> LENGTH: 23
<212> TYPE: DNA
<213> ORGANISM: Artificial
<220> FEATURE:
<223> OTHER INFORMATION: Synthesized DNA probe named PC-5

<400> SEQUENCE: 29
atacaaagag aagcgacctc gcg                                             23

<210> SEQ ID NO 30
<211> LENGTH: 25
<212> TYPE: DNA
<213> ORGANISM: Artificial
<220> FEATURE:
<223> OTHER INFORMATION: Synthesized DNA probe named PC-6

<400> SEQUENCE: 30
cggacctcat aaagtgcgtc gtagt                                           25
```

```
<210> SEQ ID NO 31
<211> LENGTH: 26
<212> TYPE: DNA
<213> ORGANISM: Artificial
<220> FEATURE:
<223> OTHER INFORMATION: Synthesized DNA probe named PC-7

<400> SEQUENCE: 31
gcggggagga agggagtaaa gttaat                                          26

<210> SEQ ID NO 32
<211> LENGTH: 28
<212> TYPE: DNA
<213> ORGANISM: Artificial
<220> FEATURE:
<223> OTHER INFORMATION: Synthesized DNA probe named PC-8

<400> SEQUENCE: 32
taacaggaag aagcttgctt ctttgctg                                        28

<210> SEQ ID NO 33
<211> LENGTH: 22
<212> TYPE: DNA
<213> ORGANISM: Artificial
<220> FEATURE:
<223> OTHER INFORMATION: Synthesized DNA probe named PC-9

<400> SEQUENCE: 33
ttgccatcgg atgtgcccag at                                              22

<210> SEQ ID NO 34
<211> LENGTH: 29
<212> TYPE: DNA
<213> ORGANISM: Artificial
<220> FEATURE:
<223> OTHER INFORMATION: Synthesized DNA probe named PC-10

<400> SEQUENCE: 34
ggaagggagt aaagttaata cctttgctc                                       29

<210> SEQ ID NO 35
<211> LENGTH: 22
<212> TYPE: DNA
<213> ORGANISM: Artificial
<220> FEATURE:
<223> OTHER INFORMATION: Synthesized DNA probe named PC-11

<400> SEQUENCE: 35
atcttttgtt gccagcggtc cg                                              22

<210> SEQ ID NO 36
<211> LENGTH: 31
<212> TYPE: DNA
<213> ORGANISM: Artificial
<220> FEATURE:
<223> OTHER INFORMATION: Synthesized DNA probe named PC-12

<400> SEQUENCE: 36
aagggagtaa agttaatacc tttgctcatt g                                    31

<210> SEQ ID NO 37
<211> LENGTH: 23
<212> TYPE: DNA
<213> ORGANISM: Artificial
<220> FEATURE:
<223> OTHER INFORMATION: Synthesized DNA probe named PD-1

<400> SEQUENCE: 37
```

```
tagcacagag agcttgctct cgg                                           23

<210> SEQ ID NO 38
<211> LENGTH: 23
<212> TYPE: DNA
<213> ORGANISM: Artificial
<220> FEATURE:
<223> OTHER INFORMATION: Synthesized DNA probe named PD-2

<400> SEQUENCE: 38
tcatgccatc agatgtgccc aga                                           23

<210> SEQ ID NO 39
<211> LENGTH: 25
<212> TYPE: DNA
<213> ORGANISM: Artificial
<220> FEATURE:
<223> OTHER INFORMATION: Synthesized DNA probe named PD-3

<400> SEQUENCE: 39
cggggaggaa ggcgataagg ttaat                                         25

<210> SEQ ID NO 40
<211> LENGTH: 25
<212> TYPE: DNA
<213> ORGANISM: Artificial
<220> FEATURE:
<223> OTHER INFORMATION: Synthesized DNA probe named PD-4

<400> SEQUENCE: 40
ttcgattgac gttacccgca gaaga                                         25

<210> SEQ ID NO 41
<211> LENGTH: 26
<212> TYPE: DNA
<213> ORGANISM: Artificial
<220> FEATURE:
<223> OTHER INFORMATION: Synthesized DNA probe named PD-5

<400> SEQUENCE: 41
ggtctgtcaa gtcggatgtg aaatcc                                        26

<210> SEQ ID NO 42
<211> LENGTH: 24
<212> TYPE: DNA
<213> ORGANISM: Artificial
<220> FEATURE:
<223> OTHER INFORMATION: Synthesized DNA probe named PD-6

<400> SEQUENCE: 42
gcaggctaga gtcttgtaga gggg                                          24

<210> SEQ ID NO 43
<211> LENGTH: 24
<212> TYPE: DNA
<213> ORGANISM: Artificial
<220> FEATURE:
<223> OTHER INFORMATION: Synthesized DNA probe named PD-7

<400> SEQUENCE: 43
tcatgccatc agatgtgccc agat                                          24

<210> SEQ ID NO 44
<211> LENGTH: 24
<212> TYPE: DNA
<213> ORGANISM: Artificial
```

```
<220> FEATURE:
<223> OTHER INFORMATION: Synthesized DNA probe named PD-8

<400> SEQUENCE: 44
cggggaggaa ggcgataagg ttaa                                           24

<210> SEQ ID NO 45
<211> LENGTH: 27
<212> TYPE: DNA
<213> ORGANISM: Artificial
<220> FEATURE:
<223> OTHER INFORMATION: Synthesized DNA probe named PD-9

<400> SEQUENCE: 45
ttatcgattg acgttacccg cagaaga                                        27

<210> SEQ ID NO 46
<211> LENGTH: 25
<212> TYPE: DNA
<213> ORGANISM: Artificial
<220> FEATURE:
<223> OTHER INFORMATION: Synthesized DNA probe named PD-10

<400> SEQUENCE: 46
cattcgaaac tggcaggcta gagtc                                          25

<210> SEQ ID NO 47
<211> LENGTH: 22
<212> TYPE: DNA
<213> ORGANISM: Artificial
<220> FEATURE:
<223> OTHER INFORMATION: Synthesized DNA probe named PD-11

<400> SEQUENCE: 47
cctttgttgc cagcggttag gc                                             22

<210> SEQ ID NO 48
<211> LENGTH: 24
<212> TYPE: DNA
<213> ORGANISM: Artificial
<220> FEATURE:
<223> OTHER INFORMATION: Synthesized DNA probe named PE-1

<400> SEQUENCE: 48
tgagggagaa agtgggggat cttc                                           24

<210> SEQ ID NO 49
<211> LENGTH: 25
<212> TYPE: DNA
<213> ORGANISM: Artificial
<220> FEATURE:
<223> OTHER INFORMATION: Synthesized DNA probe named PE-2

<400> SEQUENCE: 49
tcagatgagc ctaggtcgga ttagc                                          25

<210> SEQ ID NO 50
<211> LENGTH: 24
<212> TYPE: DNA
<213> ORGANISM: Artificial
<220> FEATURE:
<223> OTHER INFORMATION: Synthesized DNA probe named PE-3

<400> SEQUENCE: 50
gagctagagt acggtagagg gtgg                                           24
```

```
<210> SEQ ID NO 51
<211> LENGTH: 25
<212> TYPE: DNA
<213> ORGANISM: Artificial
<220> FEATURE:
<223> OTHER INFORMATION: Synthesized DNA probe named PE-4

<400> SEQUENCE: 51
gtacggtaga gggtggtgga atttc                                               25

<210> SEQ ID NO 52
<211> LENGTH: 24
<212> TYPE: DNA
<213> ORGANISM: Artificial
<220> FEATURE:
<223> OTHER INFORMATION: Synthesized DNA probe named PE-5

<400> SEQUENCE: 52
gaccacctgg actgatactg acac                                                24

<210> SEQ ID NO 53
<211> LENGTH: 25
<212> TYPE: DNA
<213> ORGANISM: Artificial
<220> FEATURE:
<223> OTHER INFORMATION: Synthesized DNA probe named PE-6

<400> SEQUENCE: 53
tggccttgac atgctgagaa ctttc                                               25

<210> SEQ ID NO 54
<211> LENGTH: 23
<212> TYPE: DNA
<213> ORGANISM: Artificial
<220> FEATURE:
<223> OTHER INFORMATION: Synthesized DNA probe named PE-7

<400> SEQUENCE: 54
ttagttacca gcacctcggg tgg                                                 23

<210> SEQ ID NO 55
<211> LENGTH: 22
<212> TYPE: DNA
<213> ORGANISM: Artificial
<220> FEATURE:
<223> OTHER INFORMATION: Synthesized DNA probe named PE-8

<400> SEQUENCE: 55
tagtctaacc gcaaggggga cg                                                  22

<210> SEQ ID NO 56
<211> LENGTH: 28
<212> TYPE: DNA
<213> ORGANISM: Artificial
<220> FEATURE:
<223> OTHER INFORMATION: Synthesized DNA probe named PE-9

<400> SEQUENCE: 56
tgcatccaaa actactgagc tagagtac                                            28

<210> SEQ ID NO 57
<211> LENGTH: 22
<212> TYPE: DNA
<213> ORGANISM: Artificial
<220> FEATURE:
<223> OTHER INFORMATION: Synthesized DNA probe named PE-10

<400> SEQUENCE: 57
```

```
gtcgactagc cgttgggatc ct                                            22
```

<210> SEQ ID NO 58
<211> LENGTH: 22
<212> TYPE: DNA
<213> ORGANISM: Artificial
<220> FEATURE:
<223> OTHER INFORMATION: Synthesized DNA probe named PF-1

<400> SEQUENCE: 58

```
tagcacaggg agcttgctcc ct                                            22
```

<210> SEQ ID NO 59
<211> LENGTH: 25
<212> TYPE: DNA
<213> ORGANISM: Artificial
<220> FEATURE:
<223> OTHER INFORMATION: Synthesized DNA probe named PF-2

<400> SEQUENCE: 59

```
aggtggtgag cttaatacgc tcatc                                         25
```

<210> SEQ ID NO 60
<211> LENGTH: 26
<212> TYPE: DNA
<213> ORGANISM: Artificial
<220> FEATURE:
<223> OTHER INFORMATION: Synthesized DNA probe named PF-3

<400> SEQUENCE: 60

```
tcatcaattg acgttactcg cagaag                                        26
```

<210> SEQ ID NO 61
<211> LENGTH: 26
<212> TYPE: DNA
<213> ORGANISM: Artificial
<220> FEATURE:
<223> OTHER INFORMATION: Synthesized DNA probe named PF-4

<400> SEQUENCE: 61

```
actgcatttg aaactggcaa gctaga                                        26
```

<210> SEQ ID NO 62
<211> LENGTH: 24
<212> TYPE: DNA
<213> ORGANISM: Artificial
<220> FEATURE:
<223> OTHER INFORMATION: Synthesized DNA probe named PF-5

<400> SEQUENCE: 62

```
ttatcctttg ttgcagcttc ggcc                                          24
```

<210> SEQ ID NO 63
<211> LENGTH: 23
<212> TYPE: DNA
<213> ORGANISM: Artificial
<220> FEATURE:
<223> OTHER INFORMATION: Synthesized DNA probe named PF-6

<400> SEQUENCE: 63

```
actttcagcg aggaggaagg tgg                                           23
```

<210> SEQ ID NO 64
<211> LENGTH: 22
<212> TYPE: DNA
<213> ORGANISM: Artificial

```
<220> FEATURE:
<223> OTHER INFORMATION: Synthesized DNA probe named PF-7

<400> SEQUENCE: 64
ggtagcacag gggagcttgc tc                                              22

<210> SEQ ID NO 65
<211> LENGTH: 26
<212> TYPE: DNA
<213> ORGANISM: Artificial
<220> FEATURE:
<223> OTHER INFORMATION: Synthesized DNA probe named PF-8

<400> SEQUENCE: 65
cgaggaggaa ggtggtgagc ttaata                                          26

<210> SEQ ID NO 66
<211> LENGTH: 26
<212> TYPE: DNA
<213> ORGANISM: Artificial
<220> FEATURE:
<223> OTHER INFORMATION: Synthesized DNA probe named PF-9

<400> SEQUENCE: 66
tacgctcatc aattgacgtt actcgc                                          26

<210> SEQ ID NO 67
<211> LENGTH: 27
<212> TYPE: DNA
<213> ORGANISM: Artificial
<220> FEATURE:
<223> OTHER INFORMATION: Synthesized DNA probe named PF-10

<400> SEQUENCE: 67
gaaactggca agctagagtc tcgtaga                                         27

<210> SEQ ID NO 68
<211> LENGTH: 24
<212> TYPE: DNA
<213> ORGANISM: Artificial
<220> FEATURE:
<223> OTHER INFORMATION: Synthesized DNA probe named PF-11

<400> SEQUENCE: 68
ttatcctttg ttgccagcgg ttcg                                            24

<210> SEQ ID NO 69
<211> LENGTH: 25
<212> TYPE: DNA
<213> ORGANISM: Artificial
<220> FEATURE:
<223> OTHER INFORMATION: Synthesized DNA probe named PG-1

<400> SEQUENCE: 69
agtagaacgc tgaaggagga gcttg                                           25

<210> SEQ ID NO 70
<211> LENGTH: 25
<212> TYPE: DNA
<213> ORGANISM: Artificial
<220> FEATURE:
<223> OTHER INFORMATION: Synthesized DNA probe named PG-2

<400> SEQUENCE: 70
cttgcatcac taccagatgg acctg                                           25
```

```
<210> SEQ ID NO 71
<211> LENGTH: 26
<212> TYPE: DNA
<213> ORGANISM: Artificial
<220> FEATURE:
<223> OTHER INFORMATION: Synthesized DNA probe named PG-3

<400> SEQUENCE: 71
tgagagtgga agttcacac tgtgac                                              26

<210> SEQ ID NO 72
<211> LENGTH: 26
<212> TYPE: DNA
<213> ORGANISM: Artificial
<220> FEATURE:
<223> OTHER INFORMATION: Synthesized DNA probe named PG-4

<400> SEQUENCE: 72
gctgtggctt aaccatagta ggcttt                                             26

<210> SEQ ID NO 73
<211> LENGTH: 23
<212> TYPE: DNA
<213> ORGANISM: Artificial
<220> FEATURE:
<223> OTHER INFORMATION: Synthesized DNA probe named PG-5

<400> SEQUENCE: 73
aagcggctct ctggcttgta act                                                23

<210> SEQ ID NO 74
<211> LENGTH: 24
<212> TYPE: DNA
<213> ORGANISM: Artificial
<220> FEATURE:
<223> OTHER INFORMATION: Synthesized DNA probe named PG-6

<400> SEQUENCE: 74 tagaccctttt ccggggttta gtgc                                              24

<210> SEQ ID NO 75
<211> LENGTH: 26
<212> TYPE: DNA
<213> ORGANISM: Artificial
<220> FEATURE:
<223> OTHER INFORMATION: Synthesized DNA probe named PG-7

<400> SEQUENCE: 75
gacggcaagc taatctctta aagcca                                             26

<210> SEQ ID NO 76
<211> LENGTH: 27
<212> TYPE: DNA
<213> ORGANISM: Artificial
<220> FEATURE:
<223> OTHER INFORMATION: Synthesized DNA probe named PG-8

<400> SEQUENCE: 76
gacatttgct taaaaggtgc acttgca                                            27

<210> SEQ ID NO 77
<211> LENGTH: 29
<212> TYPE: DNA
<213> ORGANISM: Artificial
<220> FEATURE:
<223> OTHER INFORMATION: Synthesized DNA probe named PG-9

<400> SEQUENCE: 77
```

```
gttgtaagag aagaacgagt gtgagagtg                                        29
```

<210> SEQ ID NO 78
<211> LENGTH: 24
<212> TYPE: DNA
<213> ORGANISM: Artificial
<220> FEATURE:
<223> OTHER INFORMATION: Synthesized DNA probe named PH-1

<400> SEQUENCE: 78

```
gcttgggaat ctggcttatg gagg                                             24
```

<210> SEQ ID NO 79
<211> LENGTH: 23
<212> TYPE: DNA
<213> ORGANISM: Artificial
<220> FEATURE:
<223> OTHER INFORMATION: Synthesized DNA probe named PH-2

<400> SEQUENCE: 79

```
tgccatagga tgagcccaag tgg                                              23
```

<210> SEQ ID NO 80
<211> LENGTH: 26
<212> TYPE: DNA
<213> ORGANISM: Artificial
<220> FEATURE:
<223> OTHER INFORMATION: Synthesized DNA probe named PH-3

<400> SEQUENCE: 80

```
cttgggaatg tactgacgct catgtg                                           26
```

<210> SEQ ID NO 81
<211> LENGTH: 23
<212> TYPE: DNA
<213> ORGANISM: Artificial
<220> FEATURE:
<223> OTHER INFORMATION: Synthesized DNA probe named PH-4

<400> SEQUENCE: 81

```
ggattgggct tagagcttgg tgc                                              23
```

<210> SEQ ID NO 82
<211> LENGTH: 22
<212> TYPE: DNA
<213> ORGANISM: Artificial
<220> FEATURE:
<223> OTHER INFORMATION: Synthesized DNA probe named PH-5

<400> SEQUENCE: 82

```
tacagaggga agcgaagctg cg                                               22
```

<210> SEQ ID NO 83
<211> LENGTH: 26
<212> TYPE: DNA
<213> ORGANISM: Artificial
<220> FEATURE:
<223> OTHER INFORMATION: Synthesized DNA probe named PH-6

<400> SEQUENCE: 83

```
ggcgtttacc acggtatgat tcatga                                           26
```

<210> SEQ ID NO 84
<211> LENGTH: 23
<212> TYPE: DNA
<213> ORGANISM: Artificial

```
<220> FEATURE:
<223> OTHER INFORMATION: Synthesized DNA probe named PH-7

<400> SEQUENCE: 84
aatgcctacc aagcctgcga tct                                          23

<210> SEQ ID NO 85
<211> LENGTH: 25
<212> TYPE: DNA
<213> ORGANISM: Artificial
<220> FEATURE:
<223> OTHER INFORMATION: Synthesized DNA probe named PH-8

<400> SEQUENCE: 85
tatcggaaga tgaaagtgcg ggact                                        25

<210> SEQ ID NO 86
<211> LENGTH: 22
<212> TYPE: DNA
<213> ORGANISM: Artificial
<220> FEATURE:
<223> OTHER INFORMATION: Synthesized DNA probe named PI-1

<400> SEQUENCE: 86
cagagagctt gctctcgggt ga                                           22

<210> SEQ ID NO 87
<211> LENGTH: 26
<212> TYPE: DNA
<213> ORGANISM: Artificial
<220> FEATURE:
<223> OTHER INFORMATION: Synthesized DNA probe named PI-2

<400> SEQUENCE: 87
gggaggaagg tgttgtggtt aataac                                       26

<210> SEQ ID NO 88
<211> LENGTH: 26
<212> TYPE: DNA
<213> ORGANISM: Artificial
<220> FEATURE:
<223> OTHER INFORMATION: Synthesized DNA probe named PI-3

<400> SEQUENCE: 88
ggtgttgtgg ttaataacca cagcaa                                       26

<210> SEQ ID NO 89
<211> LENGTH: 22
<212> TYPE: DNA
<213> ORGANISM: Artificial
<220> FEATURE:
<223> OTHER INFORMATION: Synthesized DNA probe named PI-4

<400> SEQUENCE: 89
gcggtctgtc aagtcggatg tg                                           22

<210> SEQ ID NO 90
<211> LENGTH: 25
<212> TYPE: DNA
<213> ORGANISM: Artificial
<220> FEATURE:
<223> OTHER INFORMATION: Synthesized DNA probe named PI-5

<400> SEQUENCE: 90
attcgaaact ggcaggctag agtct                                        25
```

```
<210> SEQ ID NO 91
<211> LENGTH: 25
<212> TYPE: DNA
<213> ORGANISM: Artificial
<220> FEATURE:
<223> OTHER INFORMATION: Synthesized DNA probe named PI-6

<400> SEQUENCE: 91
taaccacagc aattgacgtt acccg                                    25

<210> SEQ ID NO 92
<211> LENGTH: 24
<212> TYPE: DNA
<213> ORGANISM: Artificial
<220> FEATURE:
<223> OTHER INFORMATION: Synthesized DNA probe named PI-7

<400> SEQUENCE: 92
gcaattgacg ttacccgcag aaga                                     24

<210> SEQ ID NO 93
<211> LENGTH: 23
<212> TYPE: DNA
<213> ORGANISM: Artificial
<220> FEATURE:
<223> OTHER INFORMATION: Synthesized DNA probe named PI-8

<400> SEQUENCE: 93
gtagcacaga gagcttgctc tcg                                      23

<210> SEQ ID NO 94
<211> LENGTH: 23
<212> TYPE: DNA
<213> ORGANISM: Artificial
<220> FEATURE:
<223> OTHER INFORMATION: Synthesized DNA probe named PI-9

<400> SEQUENCE: 94
cggggaggaa ggtgttgtgg tta                                      23

<210> SEQ ID NO 95
<211> LENGTH: 23
<212> TYPE: DNA
<213> ORGANISM: Artificial
<220> FEATURE:
<223> OTHER INFORMATION: Synthesized DNA probe named PI-10

<400> SEQUENCE: 95
accacagcaa ttgacgttac ccg                                      23

<210> SEQ ID NO 96
<211> LENGTH: 26
<212> TYPE: DNA
<213> ORGANISM: Artificial
<220> FEATURE:
<223> OTHER INFORMATION: Synthesized DNA probe named PI-11

<400> SEQUENCE: 96
gaaactggca ggctagagtc ttgtag                                   26

<210> SEQ ID NO 97
<211> LENGTH: 22
<212> TYPE: DNA
<213> ORGANISM: Artificial
<220> FEATURE:
<223> OTHER INFORMATION: Synthesized DNA probe named PI-12

<400> SEQUENCE: 97
```

```
aggcggtctg tcaagtcgga tg                                              22

<210> SEQ ID NO 98
<211> LENGTH: 23
<212> TYPE: DNA
<213> ORGANISM: Artificial
<220> FEATURE:
<223> OTHER INFORMATION: Synthesized DNA probe named PJ-1

<400> SEQUENCE: 98
ttctttcctc ccgagtgctt gca                                             23

<210> SEQ ID NO 99
<211> LENGTH: 25
<212> TYPE: DNA
<213> ORGANISM: Artificial
<220> FEATURE:
<223> OTHER INFORMATION: Synthesized DNA probe named PJ-2

<400> SEQUENCE: 99
aacacgtggg taacctaccc atcag                                           25

<210> SEQ ID NO 100
<211> LENGTH: 24
<212> TYPE: DNA
<213> ORGANISM: Artificial
<220> FEATURE:
<223> OTHER INFORMATION: Synthesized DNA probe named PJ-3

<400> SEQUENCE: 100
atggcataag agtgaaaggc gctt                                            24

<210> SEQ ID NO 101
<211> LENGTH: 22
<212> TYPE: DNA
<213> ORGANISM: Artificial
<220> FEATURE:
<223> OTHER INFORMATION: Synthesized DNA probe named PJ-4

<400> SEQUENCE: 101
gacccgcggt gcattagcta gt                                              22

<210> SEQ ID NO 102
<211> LENGTH: 25
<212> TYPE: DNA
<213> ORGANISM: Artificial
<220> FEATURE:
<223> OTHER INFORMATION: Synthesized DNA probe named PJ-5

<400> SEQUENCE: 102
ggacgttagt aactgaacgt cccct                                           25

<210> SEQ ID NO 103
<211> LENGTH: 22
<212> TYPE: DNA
<213> ORGANISM: Artificial
<220> FEATURE:
<223> OTHER INFORMATION: Synthesized DNA probe named PJ-6

<400> SEQUENCE: 103
ctcaaccggg gagggtcatt gg                                              22

<210> SEQ ID NO 104
<211> LENGTH: 22
<212> TYPE: DNA
<213> ORGANISM: Artificial
```

```
<220> FEATURE:
<223> OTHER INFORMATION: Synthesized DNA probe named PJ-7

<400> SEQUENCE: 104
ttggagggtt ccgcccttc ag                                         22

<210> SEQ ID NO 105
<211> LENGTH: 25
<212> TYPE: DNA
<213> ORGANISM: Artificial
<220> FEATURE:
<223> OTHER INFORMATION: Synthesized DNA probe named PJ-8

<400> SEQUENCE: 105
atagagcttt cccttcgggg acaaa                                     25

<210> SEQ ID NO 106
<211> LENGTH: 29
<212> TYPE: DNA
<213> ORGANISM: Artificial
<220> FEATURE:
<223> OTHER INFORMATION: Synthesized DNA probe named PJ-9

<400> SEQUENCE: 106
cgaggtcatg caaatctctt aaagcttct                                 29

<210> SEQ ID NO 107
<211> LENGTH: 23
<212> TYPE: DNA
<213> ORGANISM: Artificial
<220> FEATURE:
<223> OTHER INFORMATION: Synthesized DNA for forward primer named F-1

<400> SEQUENCE: 107
gcggcgtgcc taatacatgc aag                                       23

<210> SEQ ID NO 108
<211> LENGTH: 23
<212> TYPE: DNA
<213> ORGANISM: Artificial
<220> FEATURE:
<223> OTHER INFORMATION: Synthesized DNA for forward primer named F-2

<400> SEQUENCE: 108
gcggcaggcc taacacatgc aag                                       23

<210> SEQ ID NO 109
<211> LENGTH: 23
<212> TYPE: DNA
<213> ORGANISM: Artificial
<220> FEATURE:
<223> OTHER INFORMATION: Synthesized DNA for forward primer named F-3

<400> SEQUENCE: 109
gcggcaggct taacacatgc aag                                       23

<210> SEQ ID NO 110
<211> LENGTH: 22
<212> TYPE: DNA
<213> ORGANISM: Artificial
<220> FEATURE:
<223> OTHER INFORMATION: Synthesized DNA for reverse primer named R-1

<400> SEQUENCE: 110
atccagccgc accttccgat ac                                        22
```

<210> SEQ ID NO 111
<211> LENGTH: 22
<212> TYPE: DNA
<213> ORGANISM: Artificial
<220> FEATURE:
<223> OTHER INFORMATION: Synthesized DNA for reverse primer named R-2

<400> SEQUENCE: 111
atccaaccgc aggttcccct ac                                           22

<210> SEQ ID NO 112
<211> LENGTH: 22
<212> TYPE: DNA
<213> ORGANISM: Artificial
<220> FEATURE:
<223> OTHER INFORMATION: Synthesized DNA for reverse primer named R-3

<400> SEQUENCE: 112
atccagccgc aggttcccct ac                                           22

<210> SEQ ID NO 113
<211> LENGTH: 26
<212> TYPE: DNA
<213> ORGANISM: Artificial
<220> FEATURE:
<223> OTHER INFORMATION: Complementary DNA Sequence of Synthesized DNA
      probe PA-1

<400> SEQUENCE: 113
tctttcactt ttgaaccatg cggttc                                       26

<210> SEQ ID NO 114
<211> LENGTH: 24
<212> TYPE: DNA
<213> ORGANISM: Artificial
<220> FEATURE:
<223> OTHER INFORMATION: Complementary DNA Sequence of Synthesized DNA
      probe PA-2

<400> SEQUENCE: 114
gcagcgcgga tccatctata agtg                                         24

<210> SEQ ID NO 115
<211> LENGTH: 26
<212> TYPE: DNA
<213> ORGANISM: Artificial
<220> FEATURE:
<223> OTHER INFORMATION: Complementary DNA Sequence of Synthesized DNA
      probe PA-3

<400> SEQUENCE: 115
ctgattaggt accgtcaaga tgtgca                                       26

<210> SEQ ID NO 116
<211> LENGTH: 22
<212> TYPE: DNA
<213> ORGANISM: Artificial
<220> FEATURE:
<223> OTHER INFORMATION: Complementary DNA Sequence of Synthesized DNA
      probe PA-4

<400> SEQUENCE: 116
cgttagctgc agcactaagg gg                                           22

<210> SEQ ID NO 117
<211> LENGTH: 23
<212> TYPE: DNA
<213> ORGANISM: Artificial

```
<220> FEATURE:
<223> OTHER INFORMATION: Complementary DNA Sequence of Synthesized DNA
      probe PA-5

<400> SEQUENCE: 117
gcggtttcgc tgcccttgt att                                              23

<210> SEQ ID NO 118
<211> LENGTH: 25
<212> TYPE: DNA
<213> ORGANISM: Artificial
<220> FEATURE:
<223> OTHER INFORMATION: Complementary DNA Sequence of Synthesized DNA
      probe PA-6

<400> SEQUENCE: 118
agctcctaaa aggttactcc accgg                                           25

<210> SEQ ID NO 119
<211> LENGTH: 25
<212> TYPE: DNA
<213> ORGANISM: Artificial
<220> FEATURE:
<223> OTHER INFORMATION: Complementary DNA Sequence of Synthesized DNA
      probe PA-7

<400> SEQUENCE: 119
tcgacggcta gctcctaaaa ggtta                                           25

<210> SEQ ID NO 120
<211> LENGTH: 23
<212> TYPE: DNA
<213> ORGANISM: Artificial
<220> FEATURE:
<223> OTHER INFORMATION: Complementary DNA Sequence of Synthesized DNA
      probe PA-8

<400> SEQUENCE: 120
accttcgacg gctagctcct aaa                                             23

<210> SEQ ID NO 121
<211> LENGTH: 23
<212> TYPE: DNA
<213> ORGANISM: Artificial
<220> FEATURE:
<223> OTHER INFORMATION: Complementary DNA Sequence of Synthesized DNA
      probe PA-9

<400> SEQUENCE: 121
atttgtccca ccttcgacgg cta                                             23

<210> SEQ ID NO 122
<211> LENGTH: 23
<212> TYPE: DNA
<213> ORGANISM: Artificial
<220> FEATURE:
<223> OTHER INFORMATION: Complementary DNA Sequence of Synthesized DNA
      probe PA-10

<400> SEQUENCE: 122
agagaagcaa gcttctcgtc cgt                                             23

<210> SEQ ID NO 123
<211> LENGTH: 25
<212> TYPE: DNA
<213> ORGANISM: Artificial
<220> FEATURE:
<223> OTHER INFORMATION: Complementary DNA Sequence of Synthesized DNA
``` probe PA-11

<400> SEQUENCE: 123
agcgcggatc catctataag tgaca                                              25

<210> SEQ ID NO 124
<211> LENGTH: 26
<212> TYPE: DNA
<213> ORGANISM: Artificial
<220> FEATURE:
<223> OTHER INFORMATION: Complementary DNA Sequence of Synthesized DNA
      probe PA-12

<400> SEQUENCE: 124
cgtcaagatg tgcacagtta cttaca                                             26

<210> SEQ ID NO 125
<211> LENGTH: 26
<212> TYPE: DNA
<213> ORGANISM: Artificial
<220> FEATURE:
<223> OTHER INFORMATION: Complementary DNA Sequence of Synthesized DNA
      probe PA-13

<400> SEQUENCE: 125
ggggaaggct ctatctctag agttgt                                             26

<210> SEQ ID NO 126
<211> LENGTH: 26
<212> TYPE: DNA
<213> ORGANISM: Artificial
<220> FEATURE:
<223> OTHER INFORMATION: Complementary DNA Sequence of Synthesized DNA
      probe PA-14

<400> SEQUENCE: 126
ggctagctcc taaaaggtta ctccac                                             26

<210> SEQ ID NO 127
<211> LENGTH: 22
<212> TYPE: DNA
<213> ORGANISM: Artificial
<220> FEATURE:
<223> OTHER INFORMATION: Complementary DNA Sequence of Synthesized DNA
      probe PB-1

<400> SEQUENCE: 127
ggagcaagct cctcgtctgt tc                                                 22

<210> SEQ ID NO 128
<211> LENGTH: 26
<212> TYPE: DNA
<213> ORGANISM: Artificial
<220> FEATURE:
<223> OTHER INFORMATION: Complementary DNA Sequence of Synthesized DNA
      probe PB-2

<400> SEQUENCE: 128
agtgacagca aaccgtctt tcacta                                              26

<210> SEQ ID NO 129
<211> LENGTH: 26
<212> TYPE: DNA
<213> ORGANISM: Artificial
<220> FEATURE:
<223> OTHER INFORMATION: Complementary DNA Sequence of Synthesized DNA
      probe PB-3

<400> SEQUENCE: 129
accgtcaaga cgtgcatagt tactta                                    26

<210> SEQ ID NO 130
<211> LENGTH: 26
<212> TYPE: DNA
<213> ORGANISM: Artificial
<220> FEATURE:
<223> OTHER INFORMATION: Complementary DNA Sequence of Synthesized DNA
      probe PB-4

<400> SEQUENCE: 130
gggaaaactc tatctctaga ggggtc                                    26

<210> SEQ ID NO 131
<211> LENGTH: 24
<212> TYPE: DNA
<213> ORGANISM: Artificial
<220> FEATURE:
<223> OTHER INFORMATION: Complementary DNA Sequence of Synthesized DNA
      probe PB-5

<400> SEQUENCE: 131
gacggctagc tccaaatggt tact                                      24

<210> SEQ ID NO 132
<211> LENGTH: 23
<212> TYPE: DNA
<213> ORGANISM: Artificial
<220> FEATURE:
<223> OTHER INFORMATION: Complementary DNA Sequence of Synthesized DNA
      probe PB-6

<400> SEQUENCE: 132
gctaacgtca gaggagcaag ctc                                       23

<210> SEQ ID NO 133
<211> LENGTH: 22
<212> TYPE: DNA
<213> ORGANISM: Artificial
<220> FEATURE:
<223> OTHER INFORMATION: Complementary DNA Sequence of Synthesized DNA
      probe PB-7

<400> SEQUENCE: 133
ccaaatggtt actccaccgg ct                                        22

<210> SEQ ID NO 134
<211> LENGTH: 22
<212> TYPE: DNA
<213> ORGANISM: Artificial
<220> FEATURE:
<223> OTHER INFORMATION: Complementary DNA Sequence of Synthesized DNA
      probe PB-8

<400> SEQUENCE: 134
cagaggagca agctcctcgt ct                                        22

<210> SEQ ID NO 135
<211> LENGTH: 29
<212> TYPE: DNA
<213> ORGANISM: Artificial
<220> FEATURE:
<223> OTHER INFORMATION: Complementary DNA Sequence of Synthesized DNA
      probe PB-9

<400> SEQUENCE: 135
acgtgcatag ttacttacac atttgttct                                    29

<210> SEQ ID NO 136
<211> LENGTH: 22
<212> TYPE: DNA
<213> ORGANISM: Artificial
<220> FEATURE:
<223> OTHER INFORMATION: Complementary DNA Sequence of Synthesized DNA
      probe PB-10

<400> SEQUENCE: 136
tcgacggcta gctccaaatg gt                                           22

<210> SEQ ID NO 137
<211> LENGTH: 22
<212> TYPE: DNA
<213> ORGANISM: Artificial
<220> FEATURE:
<223> OTHER INFORMATION: Complementary DNA Sequence of Synthesized DNA
      probe PC-1

<400> SEQUENCE: 137
tgggcacatc cgatggcaag ag                                           22

<210> SEQ ID NO 138
<211> LENGTH: 26
<212> TYPE: DNA
<213> ORGANISM: Artificial
<220> FEATURE:
<223> OTHER INFORMATION: Complementary DNA Sequence of Synthesized DNA
      probe PC-2

<400> SEQUENCE: 138
cgggtaacgt caatgagcaa aggtat                                       26

<210> SEQ ID NO 139
<211> LENGTH: 24
<212> TYPE: DNA
<213> ORGANISM: Artificial
<220> FEATURE:
<223> OTHER INFORMATION: Complementary DNA Sequence of Synthesized DNA
      probe PC-3

<400> SEQUENCE: 139
ctgcgggtaa cgtcaatgag caaa                                         24

<210> SEQ ID NO 140
<211> LENGTH: 24
<212> TYPE: DNA
<213> ORGANISM: Artificial
<220> FEATURE:
<223> OTHER INFORMATION: Complementary DNA Sequence of Synthesized DNA
      probe PC-4

<400> SEQUENCE: 140
tctacgagac tcaagcttgc cagt                                         24

<210> SEQ ID NO 141
<211> LENGTH: 23
<212> TYPE: DNA
<213> ORGANISM: Artificial
<220> FEATURE:
<223> OTHER INFORMATION: Complementary DNA Sequence of Synthesized DNA
      probe PC-5

<400> SEQUENCE: 141
cgcgaggtcg cttctctttg tat                                          23

```
<210> SEQ ID NO 142
<211> LENGTH: 25
<212> TYPE: DNA
<213> ORGANISM: Artificial
<220> FEATURE:
<223> OTHER INFORMATION: Complementary DNA Sequence of Synthesized DNA
      probe PC-6

<400> SEQUENCE: 142
actacgacgc actttatgag gtccg                                          25

<210> SEQ ID NO 143
<211> LENGTH: 26
<212> TYPE: DNA
<213> ORGANISM: Artificial
<220> FEATURE:
<223> OTHER INFORMATION: Complementary DNA Sequence of Synthesized DNA
      probe PC-7

<400> SEQUENCE: 143 attaactttta ctcccttcct ccccgc                                        26

<210> SEQ ID NO 144
<211> LENGTH: 28
<212> TYPE: DNA
<213> ORGANISM: Artificial
<220> FEATURE:
<223> OTHER INFORMATION: Complementary DNA Sequence of Synthesized DNA
      probe PC-8

<400> SEQUENCE: 144
cagcaaagaa gcaagcttct tcctgtta                                       28

<210> SEQ ID NO 145
<211> LENGTH: 22
<212> TYPE: DNA
<213> ORGANISM: Artificial
<220> FEATURE:
<223> OTHER INFORMATION: Complementary DNA Sequence of Synthesized DNA
      probe PC-9

<400> SEQUENCE: 145
atctgggcac atccgatggc aa                                             22

<210> SEQ ID NO 146
<211> LENGTH: 29
<212> TYPE: DNA
<213> ORGANISM: Artificial
<220> FEATURE:
<223> OTHER INFORMATION: Complementary DNA Sequence of Synthesized DNA
      probe PC-10

<400> SEQUENCE: 146
gagcaaaggt attaacttta ctcccttcc                                      29

<210> SEQ ID NO 147
<211> LENGTH: 22
<212> TYPE: DNA
<213> ORGANISM: Artificial
<220> FEATURE:
<223> OTHER INFORMATION: Complementary DNA Sequence of Synthesized DNA
      probe PC-11

<400> SEQUENCE: 147
cggaccgctg gcaacaaaag at                                             22

<210> SEQ ID NO 148
```

```
<211> LENGTH: 31
<212> TYPE: DNA
<213> ORGANISM: Artificial
<220> FEATURE:
<223> OTHER INFORMATION: Complementary DNA Sequence of Synthesized DNA
      probe PC-12

<400> SEQUENCE: 148
caatgagcaa aggtattaac tttactccct t                               31

<210> SEQ ID NO 149
<211> LENGTH: 23
<212> TYPE: DNA
<213> ORGANISM: Artificial
<220> FEATURE:
<223> OTHER INFORMATION: Complementary DNA Sequence of Synthesized DNA
      probe PD-1

<400> SEQUENCE: 149
ccgagagcaa gctctctgtg cta                                       23

<210> SEQ ID NO 150
<211> LENGTH: 23
<212> TYPE: DNA
<213> ORGANISM: Artificial
<220> FEATURE:
<223> OTHER INFORMATION: Complementary DNA Sequence of Synthesized DNA
      probe PD-2

<400> SEQUENCE: 150
tctgggcaca tctgatggca tga                                       23

<210> SEQ ID NO 151
<211> LENGTH: 25
<212> TYPE: DNA
<213> ORGANISM: Artificial
<220> FEATURE:
<223> OTHER INFORMATION: Complementary DNA Sequence of Synthesized DNA
      probe PD-3

<400> SEQUENCE: 151
attaacctta tcgccttcct ccccg                                     25

<210> SEQ ID NO 152
<211> LENGTH: 25
<212> TYPE: DNA
<213> ORGANISM: Artificial
<220> FEATURE:
<223> OTHER INFORMATION: Complementary DNA Sequence of Synthesized DNA
      probe PD-4

<400> SEQUENCE: 152
tcttctgcgg gtaacgtcaa tcgaa                                     25

<210> SEQ ID NO 153
<211> LENGTH: 26
<212> TYPE: DNA
<213> ORGANISM: Artificial
<220> FEATURE:
<223> OTHER INFORMATION: Complementary DNA Sequence of Synthesized DNA
      probe PD-5

<400> SEQUENCE: 153
ggatttcaca tccgacttga cagacc                                    26

<210> SEQ ID NO 154
<211> LENGTH: 24
<212> TYPE: DNA
```

```
<213> ORGANISM: Artificial
<220> FEATURE:
<223> OTHER INFORMATION: Complementary DNA Sequence of Synthesized DNA
      probe PD-6

<400> SEQUENCE: 154
cccctctaca agactctagc ctgc                                          24

<210> SEQ ID NO 155
<211> LENGTH: 24
<212> TYPE: DNA
<213> ORGANISM: Artificial
<220> FEATURE:
<223> OTHER INFORMATION: Complementary DNA Sequence of Synthesized DNA
      probe PD-7

<400> SEQUENCE: 155
atctgggcac atctgatggc atga                                          24

<210> SEQ ID NO 156
<211> LENGTH: 24
<212> TYPE: DNA
<213> ORGANISM: Artificial
<220> FEATURE:
<223> OTHER INFORMATION: Complementary DNA Sequence of Synthesized DNA
      probe PD-8

<400> SEQUENCE: 156
ttaaccttat cgccttcctc cccg                                          24

<210> SEQ ID NO 157
<211> LENGTH: 27
<212> TYPE: DNA
<213> ORGANISM: Artificial
<220> FEATURE:
<223> OTHER INFORMATION: Complementary DNA Sequence of Synthesized DNA
      probe PD-9

<400> SEQUENCE: 157
tcttctgcgg gtaacgtcaa tcgataa                                       27

<210> SEQ ID NO 158
<211> LENGTH: 25
<212> TYPE: DNA
<213> ORGANISM: Artificial
<220> FEATURE:
<223> OTHER INFORMATION: Complementary DNA Sequence of Synthesized DNA
      probe PD-10

<400> SEQUENCE: 158
gactctagcc tgccagtttc gaatg                                         25

<210> SEQ ID NO 159
<211> LENGTH: 22
<212> TYPE: DNA
<213> ORGANISM: Artificial
<220> FEATURE:
<223> OTHER INFORMATION: Complementary DNA Sequence of Synthesized DNA
      probe PD-11

<400> SEQUENCE: 159
gcctaaccgc tggcaacaaa gg                                            22

<210> SEQ ID NO 160
<211> LENGTH: 24
<212> TYPE: DNA
<213> ORGANISM: Artificial
<220> FEATURE:
```

```
<223> OTHER INFORMATION: Complementary DNA Sequence of Synthesized DNA
      probe PE-1

<400> SEQUENCE: 160
gaagatcccc cactttctcc ctca                                              24

<210> SEQ ID NO 161
<211> LENGTH: 25
<212> TYPE: DNA
<213> ORGANISM: Artificial
<220> FEATURE:
<223> OTHER INFORMATION: Complementary DNA Sequence of Synthesized DNA
      probe PE-2

<400> SEQUENCE: 161
gctaatccga cctaggctca tctga                                             25

<210> SEQ ID NO 162
<211> LENGTH: 24
<212> TYPE: DNA
<213> ORGANISM: Artificial
<220> FEATURE:
<223> OTHER INFORMATION: Complementary DNA Sequence of Synthesized DNA
      probe PE-3

<400> SEQUENCE: 162
ccaccctcta ccgtactcta gctc                                              24

<210> SEQ ID NO 163
<211> LENGTH: 25
<212> TYPE: DNA
<213> ORGANISM: Artificial
<220> FEATURE:
<223> OTHER INFORMATION: Complementary DNA Sequence of Synthesized DNA
      probe PE-4

<400> SEQUENCE: 163
gaaattccac caccctctac cgtac                                             25

<210> SEQ ID NO 164
<211> LENGTH: 24
<212> TYPE: DNA
<213> ORGANISM: Artificial
<220> FEATURE:
<223> OTHER INFORMATION: Complementary DNA Sequence of Synthesized DNA
      probe PE-5

<400> SEQUENCE: 164
gtgtcagtat cagtccaggt ggtc                                              24

<210> SEQ ID NO 165
<211> LENGTH: 25
<212> TYPE: DNA
<213> ORGANISM: Artificial
<220> FEATURE:
<223> OTHER INFORMATION: Complementary DNA Sequence of Synthesized DNA
      probe PE-6

<400> SEQUENCE: 165
gaaagttctc agcatgtcaa ggcca                                             25

<210> SEQ ID NO 166
<211> LENGTH: 23
<212> TYPE: DNA
<213> ORGANISM: Artificial
<220> FEATURE:
<223> OTHER INFORMATION: Complementary DNA Sequence of Synthesized DNA
      probe PE-7
```

<400> SEQUENCE: 166
ccacccgagg tgctggtaac taa                                           23

<210> SEQ ID NO 167
<211> LENGTH: 22
<212> TYPE: DNA
<213> ORGANISM: Artificial
<220> FEATURE:
<223> OTHER INFORMATION: Complementary DNA Sequence of Synthesized DNA
      probe PE-8

<400> SEQUENCE: 167 cgtcccccttt gcggttagac ta                                           22

<210> SEQ ID NO 168
<211> LENGTH: 28
<212> TYPE: DNA
<213> ORGANISM: Artificial
<220> FEATURE:
<223> OTHER INFORMATION: Complementary DNA Sequence of Synthesized DNA
      probe PE-9

<400> SEQUENCE: 168
gtactctagc tcagtagttt tggatgca                                      28

<210> SEQ ID NO 169
<211> LENGTH: 22
<212> TYPE: DNA
<213> ORGANISM: Artificial
<220> FEATURE:
<223> OTHER INFORMATION: Complementary DNA Sequence of Synthesized DNA
      probe PE-10

<400> SEQUENCE: 169
aggatcccaa cggctagtcg ac                                            22

<210> SEQ ID NO 170
<211> LENGTH: 22
<212> TYPE: DNA
<213> ORGANISM: Artificial
<220> FEATURE:
<223> OTHER INFORMATION: Complementary DNA Sequence of Synthesized DNA
      probe PF-1

<400> SEQUENCE: 170
agggagcaag ctccctgtgc ta                                            22

<210> SEQ ID NO 171
<211> LENGTH: 25
<212> TYPE: DNA
<213> ORGANISM: Artificial
<220> FEATURE:
<223> OTHER INFORMATION: Complementary DNA Sequence of Synthesized DNA
      probe PF-2

<400> SEQUENCE: 171
gatgagcgta ttaagctcac cacct                                         25

<210> SEQ ID NO 172
<211> LENGTH: 26
<212> TYPE: DNA
<213> ORGANISM: Artificial
<220> FEATURE:
<223> OTHER INFORMATION: Complementary DNA Sequence of Synthesized DNA
      probe PF-3

<400> SEQUENCE: 172
cttctgcgag taacgtcaat tgatga                                          26

<210> SEQ ID NO 173
<211> LENGTH: 26
<212> TYPE: DNA
<213> ORGANISM: Artificial
<220> FEATURE:
<223> OTHER INFORMATION: Complementary DNA Sequence of Synthesized DNA
      probe PF-4

<400> SEQUENCE: 173
tctagcttgc cagtttcaaa tgcagt                                          26

<210> SEQ ID NO 174
<211> LENGTH: 24
<212> TYPE: DNA
<213> ORGANISM: Artificial
<220> FEATURE:
<223> OTHER INFORMATION: Complementary DNA Sequence of Synthesized DNA
      probe PF-5

<400> SEQUENCE: 174
ggccgaagct gcaacaaagg ataa                                            24

<210> SEQ ID NO 175
<211> LENGTH: 23
<212> TYPE: DNA
<213> ORGANISM: Artificial
<220> FEATURE:
<223> OTHER INFORMATION: Complementary DNA Sequence of Synthesized DNA
      probe PF-6

<400> SEQUENCE: 175
ccaccttcct cctcgctgaa agt                                             23

<210> SEQ ID NO 176
<211> LENGTH: 22
<212> TYPE: DNA
<213> ORGANISM: Artificial
<220> FEATURE:
<223> OTHER INFORMATION: Complementary DNA Sequence of Synthesized DNA
      probe PF-7

<400> SEQUENCE: 176
gagcaagctc ccctgtgcta cc                                              22

<210> SEQ ID NO 177
<211> LENGTH: 26
<212> TYPE: DNA
<213> ORGANISM: Artificial
<220> FEATURE:
<223> OTHER INFORMATION: Complementary DNA Sequence of Synthesized DNA
      probe PF-8

<400> SEQUENCE: 177
tattaagctc accaccttcc tcctcg                                          26

<210> SEQ ID NO 178
<211> LENGTH: 26
<212> TYPE: DNA
<213> ORGANISM: Artificial
<220> FEATURE:
<223> OTHER INFORMATION: Complementary DNA Sequence of Synthesized DNA
      probe PF-9

<400> SEQUENCE: 178
gcgagtaacg tcaattgatg agcgta                                          26

<210> SEQ ID NO 179
<211> LENGTH: 27
<212> TYPE: DNA
<213> ORGANISM: Artificial
<220> FEATURE:
<223> OTHER INFORMATION: Complementary DNA Sequence of Synthesized DNA
      probe PF-10

<400> SEQUENCE: 179
tctacgagac tctagcttgc cagtttc                                        27

<210> SEQ ID NO 180
<211> LENGTH: 24
<212> TYPE: DNA
<213> ORGANISM: Artificial
<220> FEATURE:
<223> OTHER INFORMATION: Complementary DNA Sequence of Synthesized DNA
      probe PF-11

<400> SEQUENCE: 180
cgaaccgctg gcaacaaagg ataa                                           24

<210> SEQ ID NO 181
<211> LENGTH: 25
<212> TYPE: DNA
<213> ORGANISM: Artificial
<220> FEATURE:
<223> OTHER INFORMATION: Complementary DNA Sequence of Synthesized DNA
      probe PG-1

<400> SEQUENCE: 181
caagctcctc cttcagcgtt ctact                                          25

<210> SEQ ID NO 182
<211> LENGTH: 25
<212> TYPE: DNA
<213> ORGANISM: Artificial
<220> FEATURE:
<223> OTHER INFORMATION: Complementary DNA Sequence of Synthesized DNA
      probe PG-2

<400> SEQUENCE: 182
caggtccatc tggtagtgat gcaag                                          25

<210> SEQ ID NO 183
<211> LENGTH: 26
<212> TYPE: DNA
<213> ORGANISM: Artificial
<220> FEATURE:
<223> OTHER INFORMATION: Complementary DNA Sequence of Synthesized DNA
      probe PG-3

<400> SEQUENCE: 183
gtcacagtgt gaactttcca ctctca                                         26

<210> SEQ ID NO 184
<211> LENGTH: 26
<212> TYPE: DNA
<213> ORGANISM: Artificial
<220> FEATURE:
<223> OTHER INFORMATION: Complementary DNA Sequence of Synthesized DNA
      probe PG-4

<400> SEQUENCE: 184
aaagcctact atggttaagc cacagc                                         26

<210> SEQ ID NO 185
<211> LENGTH: 23
<212> TYPE: DNA
<213> ORGANISM: Artificial
<220> FEATURE:
<223> OTHER INFORMATION: Complementary DNA Sequence of Synthesized DNA
      probe PG-5

<400> SEQUENCE: 185
agttacaagc cagagagccg ctt                                           23

<210> SEQ ID NO 186
<211> LENGTH: 24
<212> TYPE: DNA
<213> ORGANISM: Artificial
<220> FEATURE:
<223> OTHER INFORMATION: Complementary DNA Sequence of Synthesized DNA
      probe PG-6

<400> SEQUENCE: 186
gcactaaacc ccggaaaggg tcta                                          24

<210> SEQ ID NO 187
<211> LENGTH: 26
<212> TYPE: DNA
<213> ORGANISM: Artificial
<220> FEATURE:
<223> OTHER INFORMATION: Complementary DNA Sequence of Synthesized DNA
      probe PG-7

<400> SEQUENCE: 187
tggctttaag agattagctt gccgtc                                        26

<210> SEQ ID NO 188
<211> LENGTH: 27
<212> TYPE: DNA
<213> ORGANISM: Artificial
<220> FEATURE:
<223> OTHER INFORMATION: Complementary DNA Sequence of Synthesized DNA
      probe PG-8

<400> SEQUENCE: 188
tgcaagtgca cctttttaagc aaatgtc                                      27

<210> SEQ ID NO 189
<211> LENGTH: 29
<212> TYPE: DNA
<213> ORGANISM: Artificial
<220> FEATURE:
<223> OTHER INFORMATION: Complementary DNA Sequence of Synthesized DNA
      probe PG-9

<400> SEQUENCE: 189
cactctcaca ctcgttcttc tcttacaac                                     29

<210> SEQ ID NO 190
<211> LENGTH: 24
<212> TYPE: DNA
<213> ORGANISM: Artificial
<220> FEATURE:
<223> OTHER INFORMATION: Complementary DNA Sequence of Synthesized DNA
      probe PH-1

<400> SEQUENCE: 190
cctccataag ccagattccc aagc                                          24

<210> SEQ ID NO 191
<211> LENGTH: 23

```
<212> TYPE: DNA
<213> ORGANISM: Artificial
<220> FEATURE:
<223> OTHER INFORMATION: Complementary DNA Sequence of Synthesized DNA
      probe PH-2

<400> SEQUENCE: 191
ccacttgggc tcatcctatg gca                                            23

<210> SEQ ID NO 192
<211> LENGTH: 26
<212> TYPE: DNA
<213> ORGANISM: Artificial
<220> FEATURE:
<223> OTHER INFORMATION: Complementary DNA Sequence of Synthesized DNA
      probe PH-3

<400> SEQUENCE: 192
cacatgagcg tcagtacatt cccaag                                         26

<210> SEQ ID NO 193
<211> LENGTH: 23
<212> TYPE: DNA
<213> ORGANISM: Artificial
<220> FEATURE:
<223> OTHER INFORMATION: Complementary DNA Sequence of Synthesized DNA
      probe PH-4

<400> SEQUENCE: 193
gcaccaagct ctaagcccaa tcc                                            23

<210> SEQ ID NO 194
<211> LENGTH: 22
<212> TYPE: DNA
<213> ORGANISM: Artificial
<220> FEATURE:
<223> OTHER INFORMATION: Complementary DNA Sequence of Synthesized DNA
      probe PH-5

<400> SEQUENCE: 194
cgcagcttcg cttccctctg ta                                             22

<210> SEQ ID NO 195
<211> LENGTH: 26
<212> TYPE: DNA
<213> ORGANISM: Artificial
<220> FEATURE:
<223> OTHER INFORMATION: Complementary DNA Sequence of Synthesized DNA
      probe PH-6

<400> SEQUENCE: 195
tcatgaatca taccgtggta aacgcc                                         26

<210> SEQ ID NO 196
<211> LENGTH: 23
<212> TYPE: DNA
<213> ORGANISM: Artificial
<220> FEATURE:
<223> OTHER INFORMATION: Complementary DNA Sequence of Synthesized DNA
      probe PH-7

<400> SEQUENCE: 196
agatcgcagg cttggtaggc att                                            23

<210> SEQ ID NO 197
<211> LENGTH: 25
<212> TYPE: DNA
<213> ORGANISM: Artificial
```

-continued

<220> FEATURE:
<223> OTHER INFORMATION: Complementary DNA Sequence of Synthesized DNA
      probe PH-8

<400> SEQUENCE: 197
agtcccgcac tttcatcttc cgata                                    25

<210> SEQ ID NO 198
<211> LENGTH: 23
<212> TYPE: DNA
<213> ORGANISM: Artificial
<220> FEATURE:
<223> OTHER INFORMATION: Complementary DNA Sequence of Synthesized DNA
      probe PI-1

<400> SEQUENCE: 198
tgcaagcact cgggaggaaa gaa                                      23

<210> SEQ ID NO 199
<211> LENGTH: 25
<212> TYPE: DNA
<213> ORGANISM: Artificial
<220> FEATURE:
<223> OTHER INFORMATION: Complementary DNA Sequence of Synthesized DNA
      probe PI-2

<400> SEQUENCE: 199
ctgatgggta ggttacccac gtgtt                                    25

<210> SEQ ID NO 200
<211> LENGTH: 24
<212> TYPE: DNA
<213> ORGANISM: Artificial
<220> FEATURE:
<223> OTHER INFORMATION: Complementary DNA Sequence of Synthesized DNA
      probe PI-3

<400> SEQUENCE: 200
aagcgccttt cactcttatg ccat                                     24

<210> SEQ ID NO 201
<211> LENGTH: 22
<212> TYPE: DNA
<213> ORGANISM: Artificial
<220> FEATURE:
<223> OTHER INFORMATION: Complementary DNA Sequence of Synthesized DNA
      probe PI-4

<400> SEQUENCE: 201
actagctaat gcaccgcggg tc                                       22

<210> SEQ ID NO 202
<211> LENGTH: 25
<212> TYPE: DNA
<213> ORGANISM: Artificial
<220> FEATURE:
<223> OTHER INFORMATION: Complementary DNA Sequence of Synthesized DNA
      probe PI-5

<400> SEQUENCE: 202
aggggacgtt cagttactaa cgtcc                                    25

<210> SEQ ID NO 203
<211> LENGTH: 22
<212> TYPE: DNA
<213> ORGANISM: Artificial
<220> FEATURE:
<223> OTHER INFORMATION: Complementary DNA Sequence of Synthesized DNA probe PI-6

<400> SEQUENCE: 203
ccaatgaccc tccccggttg ag                                              22

<210> SEQ ID NO 204
<211> LENGTH: 22
<212> TYPE: DNA
<213> ORGANISM: Artificial
<220> FEATURE:
<223> OTHER INFORMATION: Complementary DNA Sequence of Synthesized DNA
      probe PI-7

<400> SEQUENCE: 204
ctgaagggcg gaaaccctcc aa                                              22

<210> SEQ ID NO 205
<211> LENGTH: 23
<212> TYPE: DNA
<213> ORGANISM: Artificial
<220> FEATURE:
<223> OTHER INFORMATION: Complementary DNA Sequence of Synthesized DNA
      probe PI-8

<400> SEQUENCE: 205
cgagagcaag ctctctgtgc tac                                             23

<210> SEQ ID NO 206
<211> LENGTH: 23
<212> TYPE: DNA
<213> ORGANISM: Artificial
<220> FEATURE:
<223> OTHER INFORMATION: Complementary DNA Sequence of Synthesized DNA
      probe PI-9

<400> SEQUENCE: 206
taaccacaac accttcctcc ccg                                             23

<210> SEQ ID NO 207
<211> LENGTH: 23
<212> TYPE: DNA
<213> ORGANISM: Artificial
<220> FEATURE:
<223> OTHER INFORMATION: Complementary DNA Sequence of Synthesized DNA
      probe PI-10

<400> SEQUENCE: 207
cgggtaacgt caattgctgt ggt                                             23

<210> SEQ ID NO 208
<211> LENGTH: 26
<212> TYPE: DNA
<213> ORGANISM: Artificial
<220> FEATURE:
<223> OTHER INFORMATION: Complementary DNA Sequence of Synthesized DNA
      probe PI-11

<400> SEQUENCE: 208
ctacaagact ctagcctgcc agtttc                                          26

<210> SEQ ID NO 209
<211> LENGTH: 22
<212> TYPE: DNA
<213> ORGANISM: Artificial
<220> FEATURE:
<223> OTHER INFORMATION: Complementary DNA Sequence of Synthesized DNA
      probe PI-12

```
<400> SEQUENCE: 209
catccgactt gacagaccgc ct                                            22

<210> SEQ ID NO 210
<211> LENGTH: 22
<212> TYPE: DNA
<213> ORGANISM: Artificial
<220> FEATURE:
<223> OTHER INFORMATION: Complementary DNA Sequence of Synthesized DNA
      probe PJ-1

<400> SEQUENCE: 210
tcacccgaga gcaagctctc tg                                            22

<210> SEQ ID NO 211
<211> LENGTH: 26
<212> TYPE: DNA
<213> ORGANISM: Artificial
<220> FEATURE:
<223> OTHER INFORMATION: Complementary DNA Sequence of Synthesized DNA
      probe PJ-2

<400> SEQUENCE: 211
gttattaacc acaacaccatt cctccc                                       26

<210> SEQ ID NO 212
<211> LENGTH: 26
<212> TYPE: DNA
<213> ORGANISM: Artificial
<220> FEATURE:
<223> OTHER INFORMATION: Complementary DNA Sequence of Synthesized DNA
      probe PJ-3

<400> SEQUENCE: 212
ttgctgtggt tattaaccac aacacc                                        26

<210> SEQ ID NO 213
<211> LENGTH: 22
<212> TYPE: DNA
<213> ORGANISM: Artificial
<220> FEATURE:
<223> OTHER INFORMATION: Complementary DNA Sequence of Synthesized DNA
      probe PJ-4

<400> SEQUENCE: 213
cacatccgac ttgacagacc gc                                            22

<210> SEQ ID NO 214
<211> LENGTH: 25
<212> TYPE: DNA
<213> ORGANISM: Artificial
<220> FEATURE:
<223> OTHER INFORMATION: Complementary DNA Sequence of Synthesized DNA
      probe PJ-5

<400> SEQUENCE: 214
agactctagc ctgccagttt cgaat                                         25

<210> SEQ ID NO 215
<211> LENGTH: 25
<212> TYPE: DNA
<213> ORGANISM: Artificial
<220> FEATURE:
<223> OTHER INFORMATION: Complementary DNA Sequence of Synthesized DNA
      probe PJ-6

<400> SEQUENCE: 215
```

```
cgggtaacgt caattgctgt ggtta                                    25
```

<210> SEQ ID NO 216
<211> LENGTH: 24
<212> TYPE: DNA
<213> ORGANISM: Artificial
<220> FEATURE:
<223> OTHER INFORMATION: Complementary DNA Sequence of Synthesized DNA
      probe PJ-7

<400> SEQUENCE: 216

```
tcttctgcgg gtaacgtcaa ttgc                                     24
```

<210> SEQ ID NO 217
<211> LENGTH: 25
<212> TYPE: DNA
<213> ORGANISM: Artificial
<220> FEATURE:
<223> OTHER INFORMATION: Complementary DNA Sequence of Synthesized DNA
      probe PJ-8

<400> SEQUENCE: 217

```
tttgtccccg aagggaaagc tctat                                    25
```

<210> SEQ ID NO 218
<211> LENGTH: 29
<212> TYPE: DNA
<213> ORGANISM: Artificial
<220> FEATURE:
<223> OTHER INFORMATION: Complementary DNA Sequence of Synthesized DNA
      probe PJ-9

<400> SEQUENCE: 218

```
agaagcttta agagatttgc atgacctcg                                29
```